United States Patent [19]
Hanson et al.

[11] Patent Number: 5,985,307
[45] Date of Patent: Nov. 16, 1999

[54] DEVICE AND METHOD FOR NON-OCCLUSIVE LOCALIZED DRUG DELIVERY

[75] Inventors: Stephen R. Hanson, Stone Mountain; Neal A. Scott; Spencer B. King, III, both of Atlanta; Christos Markou, Dunwoody, all of Ga.

[73] Assignee: Emory University, Atlanta, Ga.

[21] Appl. No.: 08/982,537

[22] Filed: Dec. 2, 1997

Related U.S. Application Data

[63] Continuation-in-part of application No. 08/660,203, Jun. 3, 1996, Pat. No. 5,709,874, which is a continuation of application No. 08/188,248, Jan. 28, 1994, Pat. No. 5,523,092, which is a continuation-in-part of application No. 08/046,622, Apr. 14, 1993, Pat. No. 5,399,352.

[51] Int. Cl.$^6$ .................................................. A61M 25/088
[52] U.S. Cl. ........................... 424/423; 604/96; 604/101; 604/264; 604/280; 604/281
[58] Field of Search ................................. 424/423; 604/96, 604/101, 264, 280, 281

[56] References Cited

U.S. PATENT DOCUMENTS 5,256,146  10/1993  Ensminger et al. ..................... 604/104

*Primary Examiner*—Carlos A. Azpuru
*Attorney, Agent, or Firm*—Needle & Rosenberg, P.C.

[57] ABSTRACT

A device for the local delivery of a substance into a natural tissue conduit in the mammalian body. The device provides a means for locally delivering a substance into the boundary layer of fluid flowing through the conduit without substantially disrupting the fluid flow therethrough. For example, an indwelling endovascular support device is provided for delivery of a substance locally to a targeted treatment area. Also provided are methods of locally delivering a substance into a natural tissue conduit in the mammalian body utilizing the device of the present invention.

65 Claims, 7 Drawing Sheets

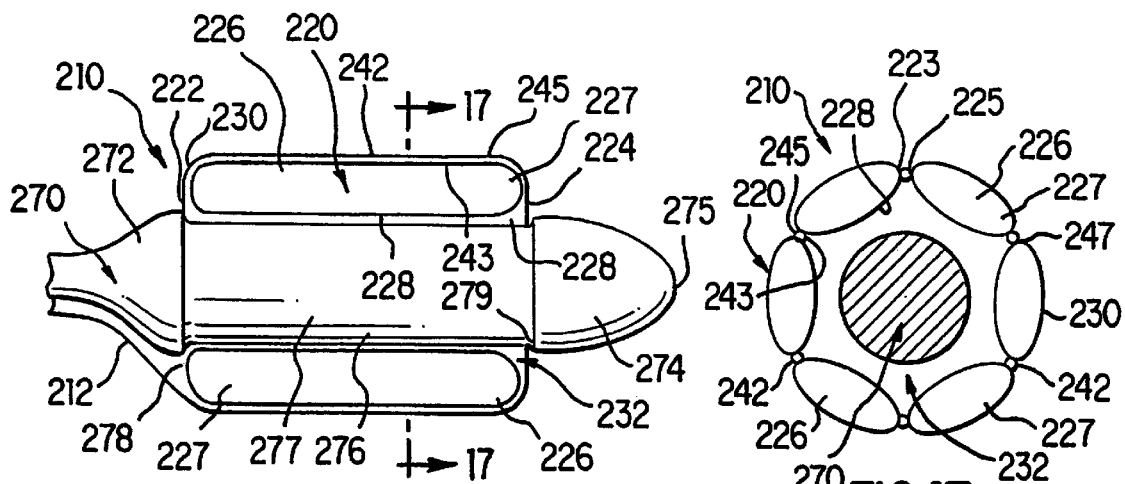
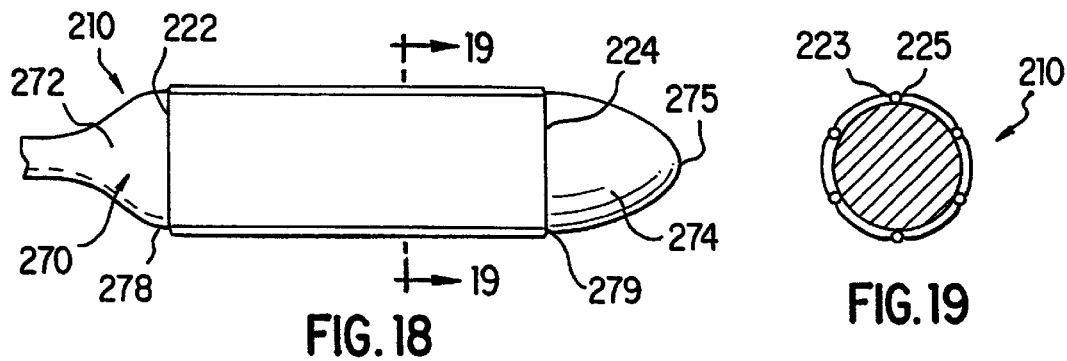
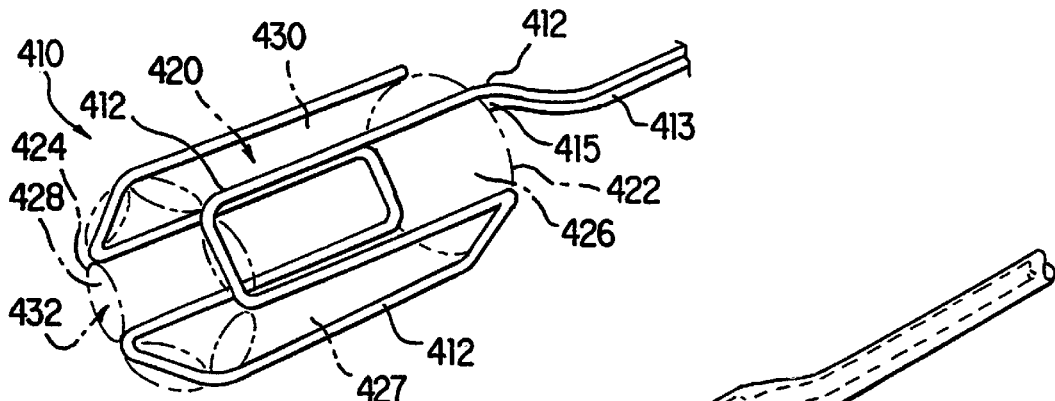
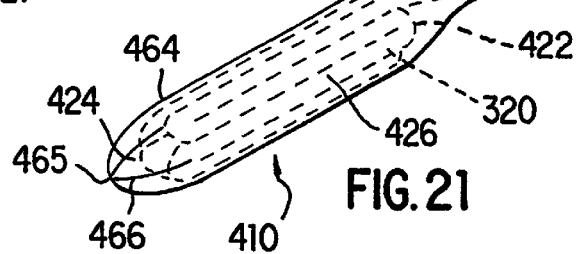

DEVICE AND METHOD FOR NON-OCCLUSIVE LOCALIZED DRUG DELIVERY

CROSS REFERENCE TO RELATED APPLICATION

This application is a continuation-in-part of now pending U.S. Ser. No. 08/660,203, filed on Jun. 3, 1996, now U.S. Pat. No. 5,709,874, which is a continuation of U.S. Ser. No. 08/188,248, filed on Jan. 28, 1994, now U.S. Pat. No. 5,523,092, which is a continuation-in-part of U.S. Ser. No. 08/046,622, filed on Apr. 14, 1993, now U.S. Pat. No. 5,399,352, the contents of which are incorporated herein by reference.

FIELD OF THE INVENTION

This invention relates to a removable device that is adapted to provide localized delivery of a substance, e.g., a therapeutic agent, to a preselected site within a natural tissue conduit such as a blood vessel, such that central fluid flow through the conduit is not substantially compromised. In particular, the invention relates a device and method for localized endovascular delivery of a drug into the boundary layer of fluid flowing through a blood vessel, thereby reducing the amount of drug needed to achieve a therapeutic concentration at a preselected site, e.g, an angioplasty site.

BACKGROUND OF THE INVENTION

One of the most complex and difficult problems that has plagued the medical profession and pharmaceutical industry for decades is the problem of achieving a therapeutic concentration of a drug locally at a target site within the body without producing unwanted systemic side effects. Parenteral or oral therapy of substances directed at treating disease in a particular internal organ must often be given in amounts dependent upon achieving critical systemic blood levels that can produce devastating side effects at other areas in the body. A prime example of a situation where local therapy is needed with drugs that also produce unwanted systemic side effects is the prevention of complications following the placement of a cardiovascular prosthetic device such as a prosthetic vascular graft, patch, or stent used to repair a damaged vessel.

Graft or stent failure is often associated with the inherent thrombogenicity of the blood contacting surface of the prosthetic device and with the body's own repair mechanisms which can lead to progressive stenotic occlusion due to neointimal fibrosis and hyperplasia. Systemic therapy aimed at preventing coagulation and thrombosis locally at the graft site is often complicated by bleeding at other sites. Likewise, systemic treatment with growth mediators or chemotherapeutic agents can produce a hyperplastic or hypoplastic response in tissue not specifically targeted. Similarly, administration of vasodilators can produce systemic hypotension.

There have been many attempts to render the vascular grafts themselves less thrombogenic, e.g., by coating the luminal surface of the graft with non-thrombogenic polymers (U.S. Pat. No. 4,687,482), cells (U.S. Pat. No. 5,037,378) or with anticoagulant drugs in a polymer coating (PCT Application WO 91/12279). Although these attempts have improved the success associated with graft placement, complications with clotting, thrombosis, and restenosis, especially that seen due to fibroplasia and smooth muscle proliferation, still abound.

Likewise, there have been many attempts to effectuate local drug delivery via endovascular means. Percutaneous transluminal coronary angioplasty (PTCA) balloon dilation catheters have been designed with coatings of drugs on the external surface of the balloon (e.g., U.S Pat. Nos. 5,102,402 and 5,199,951). Other PTCA catheters contain perforations in the wall of the PTCA balloon for infusion of drugs such as the Wolinsky catheter or the balloon within a balloon design seen in U.S. Pat. No. 5,049,132. These catheters, however, often disrupt blood flow and reduce distal tissue perfusion. Other catheters such as the Stack perfusion catheter and the catheter embodied in U.S. Pat. No. 5,181,971 were designed to facilitate drug delivery without disrupting distal tissue perfusion. These devices, however, are limited in their clinical applications, are bulky, and cannot be anchored in the vessel proximal to the targeted treatment area or utilized in non-vascular applications.

Therefore, there exists a need in the art for a means and a method of providing local therapy which can sustain high local concentrations of therapeutic drugs at a predetermined site, e.g., a site of vessel repair, without producing unwanted systemic side effects. There especially exists a need for a method and a device which can provide minimal concentrations of therapeutic agents directly to the boundary layer of blood flow near the vessel wall just proximal to a targeted treatment area which greatly reduces the amount of drug needed to achieve a therapeutic result at the target area without substantially compromising central blood flow through the vessel.

There also exists a need to provide effective local therapy for treatment of cancer and other diseases in many areas of the body such that the chemotherapy can be localized to targeted tissues, thereby minimizing the amount of drug needed for treatment and thus preventing unwanted systemic side effects from systemic administration.

SUMMARY OF THE INVENTION

The present invention satisfies the need to provide localized therapy to targeted tissues by providing a means to locally deliver a substance into any natural tissue conduit of the mammalian body and thereby provide localized therapy to targeted tissues without substantially compromising central blood flow through the vessel. Alternate embodiments of the invention can be utilized to provide local drug delivery to a predetermined site in any conduit, including but not limited to, lymphatic vessels, bile ducts, ureters, the intestinal tract, and the respiratory tree. For example, a transitional cell carcinoma of the bladder can be effectively treated with chemotherapeutic agents by insertion of the device of the present invention into a ureter and administering the appropriate drug. Substances delivered into the boundary layer of fluid flowing through the tissue conduit (near the vessel wall) greatly reduce the amount of the substance needed to achieve a therapeutic result at the target treatment area.

The devices and methods provided by the invention permit direct delivery of a substance, e.g., a drug, to the boundary layer of fluid flowing through conduit, e.g., a blood vessel, without disrupting normal fluid flow through the conduit.

In one embodiment, the drug delivery device is comprised of a low profile, indwelling endovascular support device adapted for providing prolonged localized delivery of a therapeutic agent to a preselected site within a blood vessel without substantially compromising central blood flow through the vessel. The device comprises an inflatable, elongated, tubular-shaped balloon having a proximal end, a distal end and a central lumen therethrough. The tubular-shaped balloon has an inflation chamber which is defined by a medial exterior wall and a lateral exterior wall the medial exterior wall of the inflation chamber also defines a central lumen through which blood flow and perfusion of distal tissues occurs substantially uncompromised.

The device has means for inflation of the inflation chamber and also is comprised of a therapeutic agent delivery means which can be located on a selected one of the medial exterior wall or the lateral exterior wall. In certain embodiments, the therapeutic agent delivery means can comprise a micro porous surface or a selectively permeable membrane in fluid connection with the inflation chamber for delivery of the therapeutic agent. Support means, e.g., a flexible support member, for maintaining a predetermined shape of the balloon and inflation chamber can be provided on a selected one of the medial exterior wall, the lateral exterior wall or be located within the inflation chamber.

In another embodiment, the invention provides a removable, expandable, non-occlusive, dual-chambered endovascular support device adapted for providing prolonged localized delivery of a therapeutic agent to a preselected site within a blood vessel, comprising an inflatable, elongated, tubular-shaped balloon having a proximal end, a distal end and a central lumen having medial and lateral inflation chambers therein. The medial inflation chamber is comprised of a medial exterior wall which defines the central lumen and an opposite dividing wall. The lateral inflation chamber is coaxially disposed about the medial inflation chamber is comprised of the dividing wall, and an opposite lateral exterior wall. Medial and lateral chamber inflation means are provided for selective inflation of the respective chambers and a therapeutic agent delivery means is located on a selected one of the medial exterior wall or the lateral exterior wall.

In yet another embodiment, the invention provides a removable, non-occlusive, endovascular support device adapted for prolonged localized delivery of a therapeutic agent at a preselected site within a blood vessel, comprising a tubular-shaped, dual-chambered, expandable member having a proximal end, a distal end, an exterior surface and an interior surface which defines a central lumen therethrough. One chamber is a support chamber formed from a plurality of inflatable interconnecting inflation cells. A second tubular-shaped therapeutic agent delivery chamber or tube is interspersed between the inflation cells. The therapeutic agent delivery chamber or tube is comprised of an outside surface having a medial face and a lateral face defined by the exterior and interior surfaces respectively of the tubular-shaped member. Support chamber inflation means in fluid connection with the support chamber and a therapeutic agent delivery tube in fluid connection with the therapeutic agent delivery chamber are also provided. A therapeutic agent delivery means is located on a selected one of the medial or lateral surfaces of the therapeutic agent delivery chamber. In one embodiment, the therapeutic agent delivery means comprises a selected one of the medial exterior wall or the lateral exterior wall defining a plurality of micro pores disposed therethrough.

Also provided are methods for locally delivering a substance to a predetermined site within a natural tissue conduit without substantially compromising central fluid flow through the conduit. For example, thrombus formation can be prevented at a coronary angioplasty site by delivering small amounts of an anticoagulant directly to the PTCA site utilizing the methods of and devices of the invention.

In particular, the invention provides a method for providing prolonged localized delivery of a therapeutic agent directly into the boundary layer of blood flowing through a predetermined site within in a blood vessel without substantially compromising central blood flow through the vessel comprising the steps of placing a therapeutic agent delivery device that is adapted to provide prolonged localized delivery of a therapeutic agent directly into the boundary layer of blood flowing through a predetermined site without substantially compromising central blood flow through the vessel adjacent the predetermined site; and delivering the therapeutic agent to the predetermined site via the therapeutic agent delivery device.

BRIEF DESCRIPTION OF THE DRAWINGS

FIG. 16 is a longitudinal cross-sectional view of an alternate embodiment of the endovascular local drug delivery device showing a plurality of inflated inflation cells of the inflation chamber with longitudionally extending flexible support members between the inflated inflation cells.

FIG. 17 is a cross-sectional view of the embodiment shown in FIG. 16 taken along lines 17—17 in FIG. 16.

FIG. 18 is a longitudinal cross-sectional view of the embodiment shown in FIG. 17 mounted on the deployment catheter with a plurality of deflated inflation cells of the inflation chamber having longitudionally extending flexible support members located between the inflated inflation cells.

FIG. 19 is a cross-sectional view of the embodiment shown in FIG. 18 taken along lines 19—19 in FIG. 18.

FIG. 20 is a cross-sectional view of one embodiment of the endovascular local drug delivery device of the invention showing a continuous tubular medication lumen interspersed between a plurality of inflation cells in the (inflated) expanded position.

FIG. 21 is a perspective view of the embodiment shown in FIG. 20 contained within a removable sheath (or delivery catheter) covering the device.

DETAILED DESCRIPTION OF THE ILLUSTRATIVE EMBODIMENTS

Figure 1:
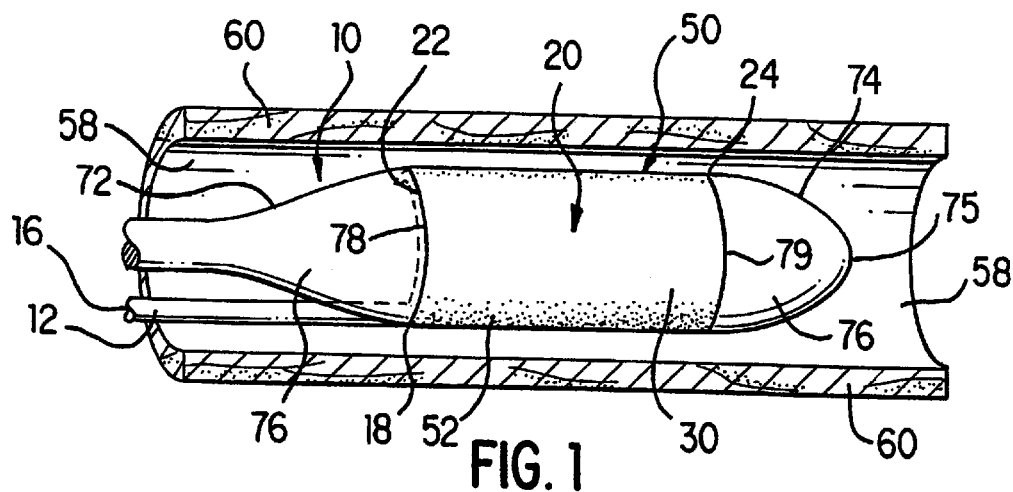
FIG. 1 is a perspective view of one embodiment showing the endovascular local drug delivery device within the lumen of a blood vessel and mounted on a deployment catheter (or stylet) prior to deployment.

The present invention may be understood more readily by reference to the following detailed description of specific embodiments and the Examples and Figures included therein.

As used in the claims, "a" can mean one or more.

The present invention provides a device that is adapted to provide for prolonged localized delivery of a substance at or to a preselected site in a natural tissue conduit in the mammalian body without substantially compromising fluid flow through the conduit. The phrase "natural tissue conduit" as used herein means any area of the mammalian body which functions to transport substances and includes, but is not limited to, e.g., blood vessels of the cardiovascular system (arteries and veins), vessels of the lymphatic system, the intestinal tract (esophagus, stomach, the small and large intestines, and colon), the portal-caval system of the liver, the gall bladder and bile duct, the urinary system (ureters, bladder and urethra), the respiratory system (trachea, bronchi, and bronchioles), and ducts and ductules connecting endocrine organs to other areas of the body. The devices of the present invention can be used in any mammal or in any animal in which natural tissue conduits are found.

In particular, the invention relates a device and method for localized endovascular delivery of a drug into the boundary layer of fluid flowing through a blood vessel, thereby reducing the amount of drug needed to achieve a therapeutic concentration at a preselected site, e.g., an angioplasty site. The devices described herein can also be referred to interchangeably as "catheters" and are designed for intraluminal (e.g., endovascular) use in the natural tissue conduits, e.g., arteries and veins of the mammalian body as set forth above.

As used herein, the phrases "preselected site" or "predetermined site" can mean any site within, or accessible by the natural tissue conduit. The preselected site can be the site where the substance delivery segment of the device is deployed (positioned) within the conduit and can include diseased as well as healthy sections of the conduit. The preselected site can be proximal (upstream) of a diseased segment of the natural tissue conduit. In particular, the preselected site can be a site selected for deployment of the substance delivery portion of the device which allows treatment of a target treatment area or organ distal (downstream) of the deployment site which is accessible for therapy via a fluid flowing through the conduit.

Depending upon the context in which used, the phrase "preselected site" can also refer to the location within the lumen of the conduit (relative to the cross-sectional diameter thereof) at which a substance is delivered into the lumen of the conduit. For example, the preselected site can be the boundary layer or rim flow layer of a fluid flowing through the conduit. As used herein, the "boundary layer" or "rim flow layer" typically comprises an annular ring at the fluid-conduit interface which occupies only between about 1% and about 10%, but especially about 5% of the conduit cross-sectional area. As can be appreciated by one of skill in the art, the size of the boundary layer can vary depending upon the size of the vessel, blood flow conditions and drug diffusivity. Thus, "boundary layer" and "brim flow layer" are used interchangeably herein.

The phrase "target treatment area" is meant to include any area intended to receive a beneficial or therapeutic effect of a substance administered by the devices described herein. For example, the target treatment area can be a stenotic lesion in a blood vessel, a developing thrombus, a PTCA site, a localized tumor or the like. In particular, the target treatment area can be the preselected site.

Referring generally now to FIGS. 1–3, and FIGS. 7–9, the first embodiment of the invention comprises a removable and expandable, non-occlusive endovascular support device 10 that is adapted for providing prolonged localized delivery of a therapeutic agent to a preselected site within a blood vessel 60. The device is further comprised of a body portion which is comprised of an inflatable, elongated, tubular-shaped balloon 20. The inflatable balloon 20 has a proximal end 22, a distal end 24 and a single lumen inflation chamber 26. The inflation chamber 26 is further defined by a medial exterior wall 28 and an opposite lateral exterior wall 30 which join at the opposed proximal and distal ends 22, 24 to form the inflation chamber 26.

Figure 3:
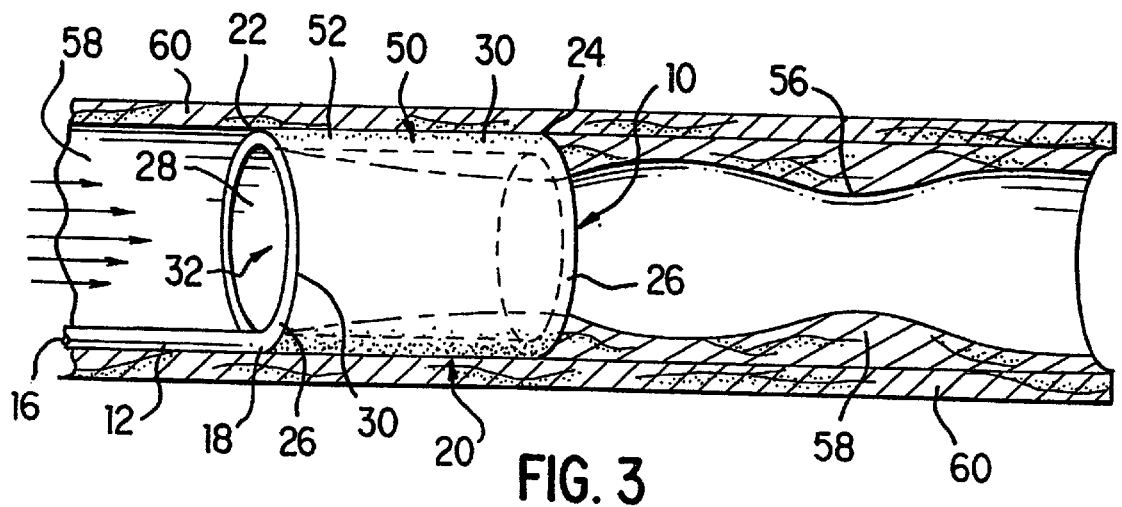
FIG. 3 shows one embodiment of the endovascular drug delivery device deployed upstream of a predetermined treatment site. e.g., a thrombotic lesion or restenosing PTCA site.

The medial exterior wall 28 further defines a hollow central lumen 32 of inflatable balloon 20. In the deployed configuration, as shown in FIG. 3, and set forth in gerater detail below, central lumen 32 allows for the blood to flow through blood vessel 60 substantially uncompromised.

Chamber inflation means is provided which is in fluid connection with inflation chamber 26. In the embodiment shown in FIGS. 1–3 chamber inflation means is comprised of a low profile elongated flexible tube 12 of a predetermined length and diameter and having a proximal end (not shown) which opens and communicates with lumen 16 of tube 12 and a distal end 18 which is in fluid communication with inflation chamber 26. The length and the diameter of tube 12 will vary, of course, depending upon the size of the blood vessel and the distance between the point of entry therein and the preselected site site where balloon 20 of device 10 is to be deployed. For example, a typical length for a catheter designed for intracardiac deployment via the femoral artery in a human adult can be between about 80 and 200 cm long with an inside tube diameter of between about 1.0 and 4.5 mm, whereas a catheter designed for use in the proximal urethra of an adult male would be between about 5 and 40 cm long and about 0.1 and 3.0 mm in diameter.

Therapeutic agent delivery means 50 are provided on a selected one of the medial exterior wall 28 or the lateral exterior wall 30 depending upon the desired location of the preselected site. In the embodiment shown in FIG. 3, for example, the therapeutic agent delivery means 50 is located on the lateral exterior wall 30. A substance, e.g., a fluid containing a drug or other therapeutic agent, can be delivered to inflation chamber 26 under a predetermined amount of pressure such that the fluid reaches the therapeutic agent delivery means located on either the medial or lateral exterior walls 28, 30 and is then delivered via said delivery means to the preselected site.

Means for delivering the device 10 to the preselected site are also provided by the invention. In the embodiment shown in FIGS. 1–2, a guidewire or delivery stylet 70 is adapted to be removably disposed through the central lumen 32, and is comprised of a proximal end or tip (not shown), a proximally located neck portion 72 and a distally located head portion 74 which terminates in tip 75. Middle portion 76 interconnects neck portion 72 and head portion 74. Retaining means are located on the middle portion 76 for removably securing device 10 to stylet 70.

Figure 2:
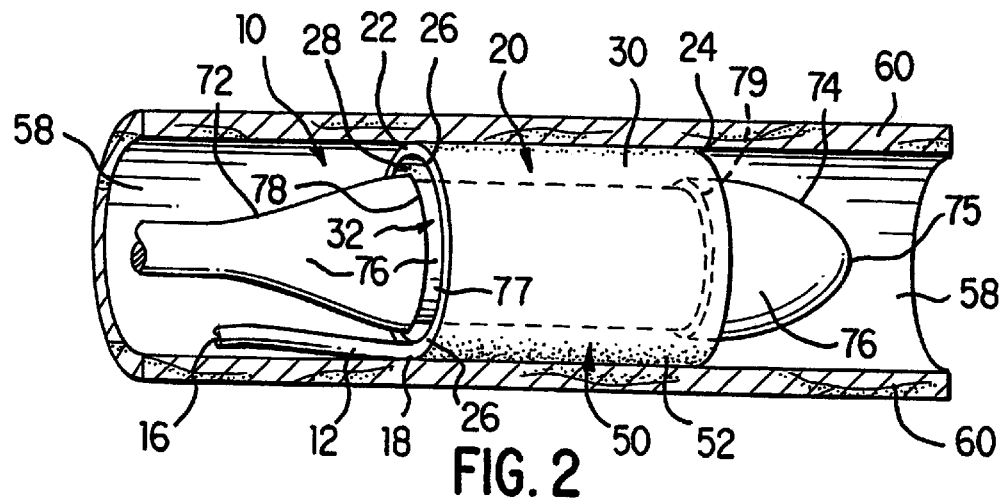
FIG. 2 is a perspective view of the embodiment shown in FIG. 1 showing the endovascular local drug delivery device during deployment within the lumen of a blood vessel with the inflation chamber inflated to allow for removal of the deployment catheter

Referring to FIG. 2, the retaining means on the middle portion 76 of stylet 10 can comprised of a central body 77 which terminates in retaining shoulders 78, 79 at the respective proximal and distal ends of middle portion 76. Central body 77 of the middle portion 76 has a diameter slightly less than the diameters of retaining shoulders 78, 79 which retain the device 10 on the delivery stylet 70 in the deflated or pre-deployed state as shown in FIG. 1.

It is desired that the guidewire or delivery stylet 70 be of a low profile and constructed from a material of sufficient stiffness to allow the surgeon to advance the stylet 70 and device 10 through the lumen of blood vessel 60 to the predetermined site for delivery. The stylets described herein can be constructed from any of a number of biocompatable materials including, but not limited to metals such as stainless steel, metal alloys, and plastics or polymers.

It is also contemplated that the the delivery means for the device 10 shown in FIGS. 1–2 can further comprise a hollow delivery sheath (similar to sheath 464 shown in FIG. 21) of sufficient diameter so as to slidably cover at least the middle portion 76 of the stylet 70. In one embodiment it is preferred that the delivery sheath cover all but the proximal end (not shown) and head portion 74 of stylet 70. If desired, a second retaining shoulder (not shown) sized complimentarily to the diameter of the retaining sheath can be located on head portion 74 so as to limit forward movement of the sheath toward distal tip 75.

Means for controlling the stylet 70 and the optional sheath can be located adjacent the proximal end or tip (not shown) of stylet 70. Such means can simply comprise the proximal ends of the stylet and/or sheath which are located outside the patient's body to allow the surgeon to advance the stylet 70, device 10 and optional sheath (not shown) to the predetermined site. Once advancement of the stylet 70 and preloaded device 10 (see, FIG. 1) to the predetermined site has occured, deployment of the device can occur by injecting a fluid into the lumen 16 of flexible tube 12 under sufficient pressure to inflate and expand the inflation chamber 26 of device 10 (see, FIG. 2). Of course, if the optional sheath is in place over the device 10 it must first be withdrawn proximally away from the predetermined site and preferrably removed from the patient's body.

Inflation of inflation chamber 26 allows the lateral exterior wall 30 to come into retaining contact with the luminal surface 58 of vessel 60 adjacent the predetermined or desired delivery site and the physician can then retract stylet 70 out of the patient's body leaving the device 10 deployed as shown in FIG. 3.

Briefly, once the device 10 is deployed within blood vessel 60, the physician introduces a fluid containing the therapeutic agent into the lumen 16 of tube 12 adjacent the proximal end (not shown) of the tube 12. The chamber inflation means which delivers the fluid containing the therapeutic agent to the inflation chamber 26 via tube 12 is in fluid connection with tube 12 at distal end 18. Tube 12 extends from its fluid connection with inflation chamber 26 at distal end 18 proximally in the arterial tree via the femoral artery such that the proximal end (not shown) of tube 12 remains outside of the patient's body and within easy access of the physician.

As the skilled artisan can appreciate, (in the treatment of coronary artery disease, for example) the fluid containing a desired substance, e.g., a drug, can be introduced into the lumen 16 of tube 12 and subsequently into the inflation chamber 26 and out into the boundary layer via therapeutic agent delivery means by any of a number of possible methods. The fluid can be introduced under pressure directly into an appropriately configured opening (not shown) defined by the proximal end of tube 12. For example, an infusion port can be utilized at the proximal end of tube 12 for connection of a remote fluid delivery source. As can be appreciated by one of skill in the art, the infusion port can have any of a number of possible configurations for connection of the remote substance source including, but not limited to, luer lock connectors, snaplock connectors, injection sites, and valved connectors.

Figure 9:
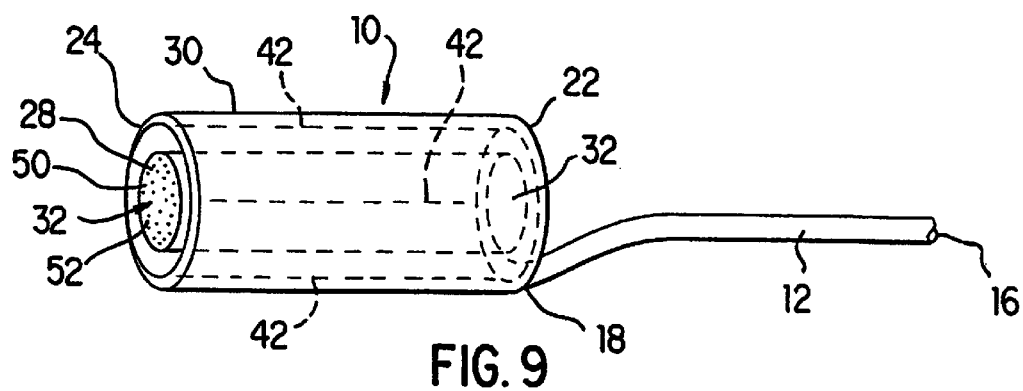
FIG. 9 is a perspective view of the embodiment shown in FIGS. 7–8 showing the endovascular local drug delivery device with the inflation chamber inflated and the deployment catheter removed. Micropores are shown on the medial exterior wall for delivery of a therapeutic agent directly into the boundary layer of fluid flowing through the central lumen.

In a preferred embodiment, as depicted in FIG. 3 the therapeutic agent delivery means 50 can comprise a plurality of micropores 52 located in the lateral exterior wall 30 for therapeutic agent delivery directly into the luminal surface of the blood vessel 60 at the deployment site. Alternatively, (as shown in FIG. 9) micropores 52 can be positioned in the medial exterior wall 28 for delivery of the therapeutic agent directly into the boundary layer of blood flowing through the blood vessel (i.e., the layer of fluid flow adjacent the luminal surface 58 of the blood vessel 60) for delivery to a preselected site distal to the deployment site when the blood vessel is an artery.

Depending upon the size or number of pores, the delivery rate (pressure) of the fluid and ultimately the amount of therapeutic agent can be controlled to achieve a desired effect. Typically the pores for the devices described herein can range in size from about 100 nm to about 1 mm. The choice of material for the exterior wall construction, will influence the size of the micro pores. For example, an exterior wall comprised of polyethelene could have a micropore size of 1 to 100 microns depending upon the intended application for the device. These pores can be made by any of a number of methods including, but not limited to, mechanical drilling, lazar or ion etching, or membrane casting.

Alternatively, the therapeutic agent delivery means can comprise a selectively permeable membrane located on a selected one of the medial exterior wall 28 or the lateral exterior wall 30.

The micropores 52 can also be configured in any of a variety of shapes. In the embodiment shown in FIGS. 1–3, the micropores 52 are round, however, they can also be configured as slit openings which normally remain closed unless fluid 25 is being infused into the inflation chamber 26 under a predetermined amount of pressure. If desired, micropores 52 can also be configured as rectangular openings and the like.

Referring again to FIGS. 1–3, an alternative embodiment of the invention provides the therapeutic agent delivery means 50 as a selectively permeable membrane comprising at least a portion of a selected one of the medial exterior wall 28 or the lateral exterior wall 30. In one embodiment contemplated by the invention, the selectively permeable membrane is located on at least a portion of the lateral exterior wall 30 such that the membrane is juxtaposed to the luminal surface 58 of blood vessel 60 such that therapeutic agent delivery therethrough is directly into contact with the luminal wall at the deployment site. In another embodiment, the selectively permeable membrane is located on at least a portion of the medial exterior wall 28 such that therapeutic agent delivery therethrough is directly into the boundary layer of blood flowing through the blood vessel 60 adjacent the luminal surface 58.

The selectively permeable membranes of the invention can be constructed from a suitable biodegradable polymer, non-biodegradable polymer, nylon or selectively porous metal alloy. Examples of suitable non-biodegradable polymers include, e.g., polyurethane, polyethylene, polyethylene terephthalate, polytetrafluoroethylene, ethylene vinyl acetate, polyimid, and nylon. Examples of suitable biodegradable polymers include, polylactic acid and polyglycolic acid. Examples of suitable selectively permeable porous metal alloys include, but are not limited to stainless steel, nitinol, tantalum and platinum.

The delivery of a fluid containing a therapeutic agent to the predetermined site can occur at a preselected rate through the selectively permeable membrane. The preselected rate will very depending upon the permeability of the selectively permeable membrane for the substance of choice and upon the pressure of the infuse of the infused fluid which is applied to the upstream side of the membrane, i.e., from within the inflation chamber 26. The preselected rate can be any flow rate but will typically be between about 0.01 and 1.0 ml/minute.

In the embodiment shown in FIG. 3 the endovascular support device 10 of the invention is shown as fully deployed in a blood vessel 60 just upstream or proximal of the predetermined site 56 which is depicted in FIG. 3 as a stenotic area of blood vessel 60, e.g, a restenosing angioplasty site. Micorpores 52 of the therapeutic agent delivery means are located on the lateral exterior wall 30 of tubular shaped balloon 20 such that a therapeutic agent is delivered through micropores 52 directly into the luminal surface 58 of blood vessel 60. Alternatively, when boundary layer drug delivery is desired, micropores 52 can be positioned on the medial exterior wall 28 (as shown in FIG. 9) such that the therapeutic agent is delivered directly into the boundary layer of blood (depicted by arrows) flowing through the blood vessel 60 and central lumen 32 of device 10.

Still referring to FIGS. 1–3, device 10 can further comprise support means for maintaining a predetermined shape of the generally tubular shaped balloon 20. The support means can be located within a selected one of the medial exterior wall 28, the lateral exterior wall 30 or located within inflation chamber 26. In a preferred embodiment, support means further comprises a flexible support member 42 (shown in FIG. 9) of suitable stiffness so as to maintain the device 10 in the predetermined shape upon deployment of the device at the preselected site.

In particular, the flexible support member 42 can be comprised of any of a number of materials including, but not limited to a metal, a plastic, a polymer, and a ceramic. The flexible support member 42 can extend longitudinally or radially within a selected one of medial exterior wall 28, the lateral exterior wall 30 or reside within the lumen of inflation chamber 26. As the skilled artisan can appreciate, the flexible support member 42 can be a a slightly thickened area of the of the selected wall 28, 30 such that said support member 42 has an elasticaty that is less than the remaining portions of the selected wall 28, 30.

Alternatively, the flexible support member 42 can be be constructed from a different material as long as the flexible support member is has sufficient elasticity and pliability to allow for configuration of the device for delivery to the predetermined site and yet is capable of maintaining the desired level of support for maintaining the device 10 in the predetermined shape after deployment.

In one embodiment, the selected wall 28, 30 is comprised of a biocompatible elastic polymer, e.g., polyurethane and the flexible support member 42 is comprised of a thin strip of a suitable memory metal such as nitinol. It can be appreciated that the flexible support members 42 can be configured so as to control expansion of a selected one of the medial or lateral exterior walls 28, 30.

In one embodiment of the invention, the medial exterior wall 28 is constructed so as to expand to a predetermined length and/or diameter in response to a preselected amount of an inflation fluid pressure applied to the inflation chamber by the chamber inflation means. In other embodiment, the lateral exterior wall 30 is constructed so as to expand to a predetermined length and/or diameter in response to a preselected amount of inflation fluid pressure applied to the inflation chamber by the chamber inflation means. Thus, depending upon the particular application for which the device 10 is to be used, the skilled artisan can appreciate that the overall expansile length and diameter of device 10 can be controlled as well as the size and shape of inflation chamber 26 and central lumen 32.

In particular, the inflation chamber 26 can be constructed so as to inflate to a predetermined length along a longitudinal axis of device 10 (as defined by the central lumen 32) in response to a preselected amount of inflation fluid pressure applied to the inflation chamber 26 by the chamber inflation means. Alternatively, inflation chamber 26 can be constructed so as to inflate to a predetermined diameter along the longitudinal axis of device 10 in response to a preselected amount of inflation fluid pressure applied to the inflation chamber 26 by the chamber inflation means. Thus, the skilled artisan can appreciate that, given the teachings of the invention, expansion of the inflation chamber 26 to the predetermined length can be controlled by a controlling the expansion characteristics of a selected one of the medial exterior wall 28, the lateral exterior wall 30 or a via support means for maintaining a predetermined shape of the balloon 20 located within a selected one of the material exterior wall 28, the lateral exterior wall 30 or the inflation chamber 26. It is specifically contemplated by the invention that a selected medial or lateral exterior wall 28, 30 can be constructed to be of a predetermined length and a preselected coefficient of elasticity.

Figure 4:
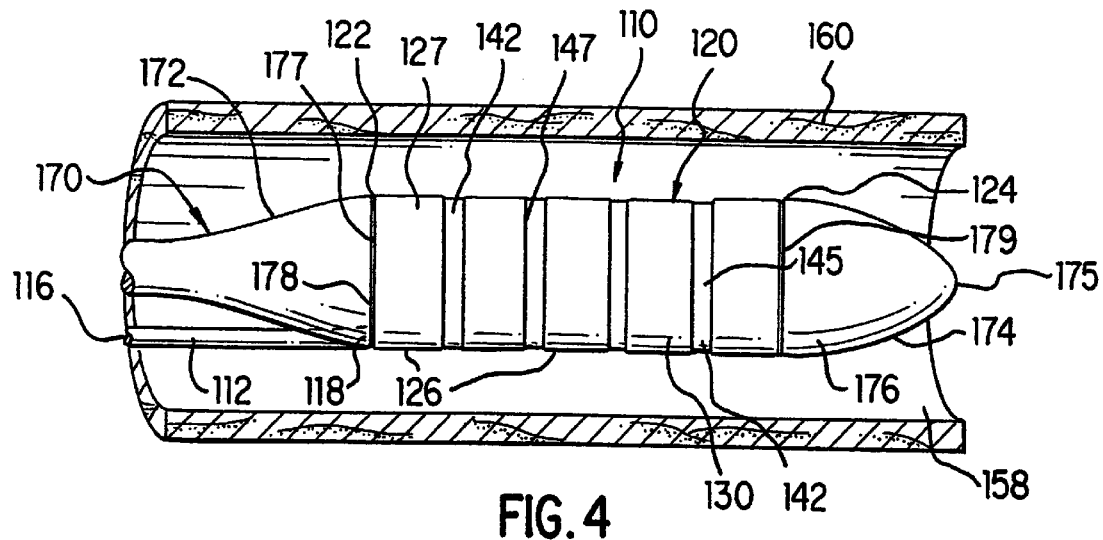
FIG. 4 is a perspective view of the one embodiment of the present invention showing the endovascular local drug delivery device within the lumen of a blood vessel and mounted on a deployment catheter (or stylet) prior to deployment.
Figure 5:
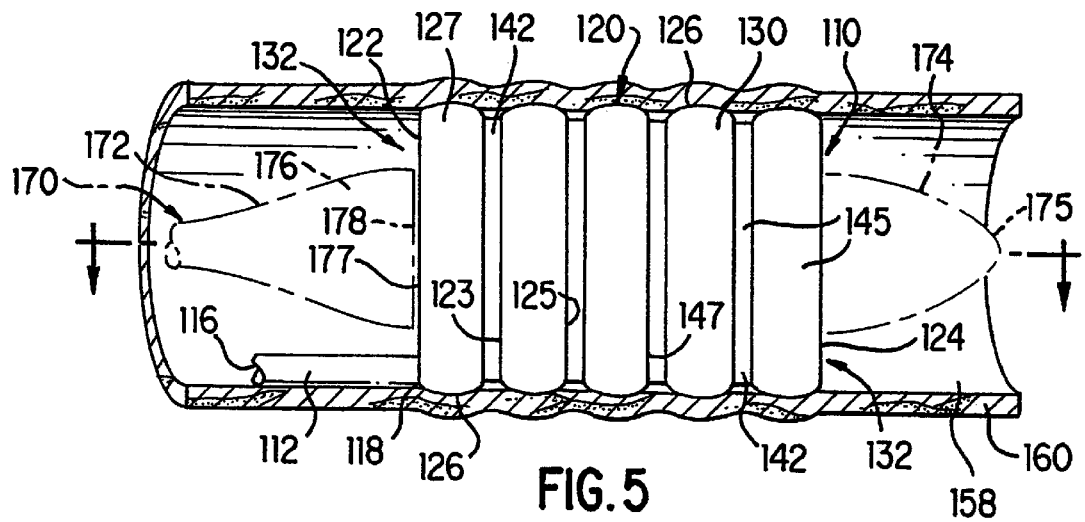
FIG. 5 is a perspective view of the embodiment shown in FIG. 4 showing the endovascular local drug delivery device during deployment within the lumen of a blood vessel with the inflation chamber inflated to allow for removal of the deployment catheter.
Figure 6:
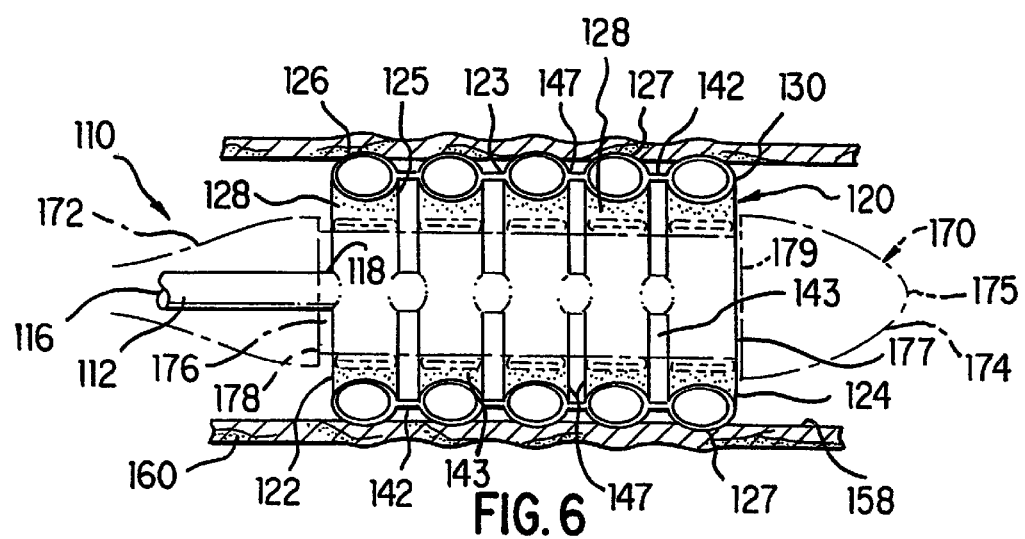
FIG. 6 is a cross-sectional view of the embodiment shown on FIG. 5 taken along lines 6—6 in FIG. 5.
Figure 7:
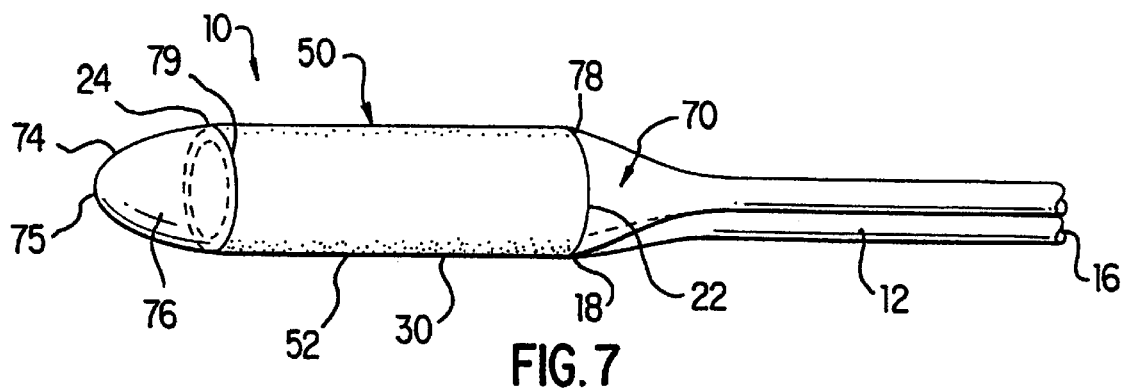
FIG. 7 is a perspective view of the embodiment of the present invention shown in FIGS. 1–3 with the endovascular local drug delivery device mounted on a deployment catheter (or stylet) prior to deployment.
Figure 8:
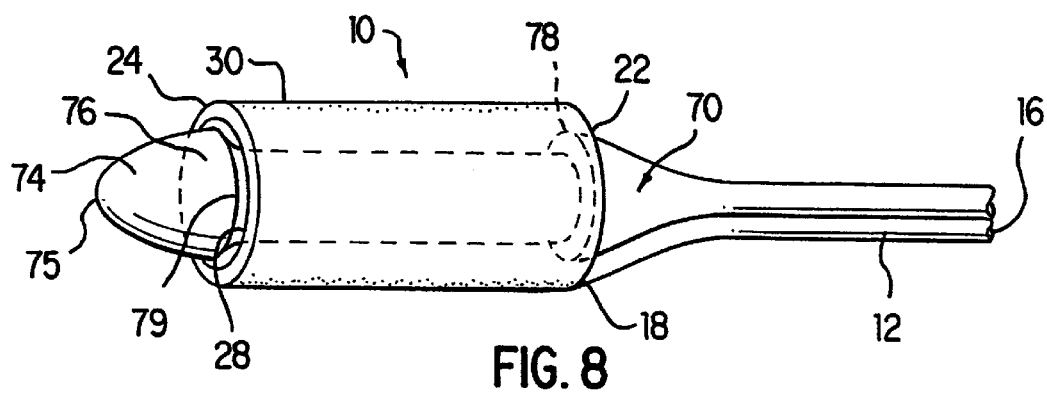
FIG. 8 is a perspective view of the embodiment shown in FIG. 7 showing the endovascular local drug delivery device with the inflation chamber inflated to allow for removal of the deployment catheter (or stylet).

Referring now to FIGS. 4–6, in another embodiment of the invention, device 110 is configured such that inflation chamber 126 further comprises a plurality of radially extending interconnected inflation cells 127 disposed among a plurality of substantially non-expandable support members 142 having a predetermined length and stiffness. The single lumen device 110 shown in FIGS. 4–6 is adapted to provide a removable and expandable, non-occlusive endovascular support device capable of providing prolonged localized delivery of a therapeutic agent to a preselected site within blood vessel 160. Device 110 is comprised of a body portion having an inflatable, elongated balloon portion 120. The inflatable balloon 120 has a proximal end 122, a distal end 124 and a single lumen inflation chamber 126 made up of a plurality of radially extending interconnected inflation cells 127.

Each inflation cell 127 of inflation chamber 126 is defined by a medial exterior wall 128 and an opposite lateral exterior wall 130 which are sealingly connected along their respective opposed proximal and distal margins 123, 125 to form the inflation cell 127 of inflation chamber 126. Support members 142 are defined by medial and lateral surfaces 143, 145 and edges 147. Support members 142 are interspersed between inflation cells 127 and are connected to the inflation cells 127 along edges 147 of support members 142 at the proximal and distal margins 123, 125 of inflation cells 127.

The medial exterior wall 128 and medial surface 143 of the inflation cells 127 and support members 142 respectively defines a hollow central lumen 132 of elongated balloon portion 120 shown in FIG. 5. In the deployed configuration, as shown in FIGS. 5–6 central lumen 132 allows for the blood to flow through blood vessel 160 substantially uncompromised and or unobstructed.

Chamber inflation means is provided and is in continuous fluid connection with inflation cells 127 of inflation chamber 126. In the embodiment shown in FIGS. 4–6 chamber inflation means is comprised of a low profile elongated flexible tube 112 of a predetermined length and diameter and having a proximal end (not shown) which opens and communicates with lumen 116 of tube 112 and a distal end 118 which is in fluid communication with inflation chamber 126. As set forth above, the length and the diameter of tube 112 can vary depending upon the size of the blood vessel or other tissue conduit in which the device is to be deployed. Further, the length and the diameter of tube 112 can vary depending upon the distance between the point of entry into the vessel or conduit and the preselected site site where device 110 is to be deployed.

Still referring to FIGS. 4–6 (as set forth above for the embodiment shown in FIGS. 1–3), therapeutic agent delivery means are provided on a selected one of the medial exterior wall 128 or the lateral exterior wall 130 of inflation cells 127 depending upon the desired location of therapeutic agent delivery and the preselected site. A fluid containing a drug or other therapeutic agent, can be delivered to inflation chamber 126 under a predetermined amount of pressure such that the fluid reaches the therapeutic agent delivery means located on either the medial or lateral exterior walls 128, 130 and is then delivered via said delivery means to the predselected site.

In the embodiment shown in FIG. 6, for example, the therapeutic agent delivery means is located on the medial exterior wall 128 of inflation cells 127 and provides for localized delivery of the therapeutic agent directly into the boundary layer of fluid flowing through vessel 160.

Means for delivering the device 110 to the preselected site are also provided. In the embodiment shown in FIGS. 4–6, a guidewire or delivery stylet 170 is adapted to be removably disposed through the central lumen 132 and is comprised of a proximal end or tip (not shown), a proximally located neck portion 172 and a distally located head portion 174 which terminates in tip 175. Middle portion 176 interconnects neck portion 172 and head portion 174. Retaining means are located on the middle portion 176 for removably securing device 110 to stylet 170.

Referring to FIG. 6, the retaining means on the middle portion 176 of stylet 110 can comprised of a central body 177 which terminates in retaining shoulders 178, 179 at the respective proximal and distal ends of middle portion 176. Central body 177 of the middle portion 176 has a diameter slightly less than the diameters of retaining shoulders 178, 179 which retain the device 110 on the delivery stylet 170 in the deflated or pre-deployed state as shown in FIG. 4.

It is desired that the guidewire or delivery stylet 170 be of a low profile and constructed from a material of sufficient stiffness to allow the surgeon to advance the stylet 170 and device 110 through the lumen of blood vessel 160 to the predetermined site for delivery.

It is also contemplated that the the delivery means for the device 110 shown in FIGS. 4–6 can further comprise a hollow delivery sheath (similar to sheath 464 shown in FIG. 21) and described above with respect to the embodiments shown in FIGS. 1–3.

Means for controlling the stylet 170 and the optional sheath can be located adjacent the proximal end or tip (not shown) of stylet 170. Such means can simply comprise the proximal ends of the stylet and or sheath which are located outside the patient's body to allow the surgeon to advance the stylet 170, device 110 and optional sheath (not shown) to the predetermined site. Once advancement of the stylet 170 and preloaded device 110 (see, FIG. 6) to the predetermined site has occured, deployment of the device can occur by injecting a fluid into inflation chamber 126 via flexible tube 112 which is sufficient to inflate and expand the of device 110 as shown in(see, FIG. 5).

Inflation of inflation chamber 126 allows the lateral exterior walls 130 of inflation cells 127 to come into retaining contact with the luminal surface 158 of vessel 160 adjacent the predetermined delivery site. Following inflation of the inflation chamber 126 the physician can then remove stylet 170 from the patient's body leaving the device 110 deployed a at the predetermined site.

For treatment of a target treatment area adjacent the delivery site, the physician can utilize fluid containing a desired substance, e.g., a drug or other therapeutic agent. The fluid can be introduced into the lumen 116 of tube 112 and subsequently into the inflation chamber 126 and out into the boundary layer via therapeutic agent delivery means by any of a number of possible methods. The fluid can be introduced under pressure directly into an appropriately configured opening (not shown) defined by the proximal end of tube 112. For example, an infusion port can be utilized at the proximal end of tube 112 for connection of a remote fluid delivery source. As can be appreciated by one of skill in the art, the infusion port for all devices described herein can have any of a number of possible configurations for connection of the remote substance source including, but not limited to, luer lock connectors, snaplock connectors, injection sites, and valved connectors.

In a preferred embodiment, as depicted in FIG. 6, the therapeutic agent delivery means can comprise a plurality of micropores 152 (or a selectively permeable membrane) located in the medial exterior walls 128 of inflation cells 127 for therapeutic agent delivery directly into the boundary layer of blood flowing through vessel 160. Alternatively, if the micropores or the selectively permeable membrane are located on the lateral surfaces 130 of inflation cells 127 therapeutic agent delivery will be directly into the luminal surface 158 of blood vessel 160 at the deployment site.

Depending upon the size or number of pores, (or the permeability of the membrane) the delivery rate (pressure) of the fluid and concentration of the therapeutic agent, the amount of therapeutic agent delivery can be precisely controlled to achieve a desired effect.

Referring now to FIGS. 16–19, an alternate embodiment of the invention is provided which wherein the inflation chamber 226 further comprises a plurality of longitudinally extending interconnected inflation cells 227 disposed among a plurality of substantially non-expandable longitudionally extending support members 242 having a predetermined length and stiffness. The single lumen device 210 shown in FIGS. 16–19 is adapted to provide a removable and expandable, non-occlusive endovascular support device capable of providing prolonged localized delivery of a therapeutic agent to a preselected site within blood vessel. Device 210 is comprised of a body portion having an inflatable, elongated balloon portion 220. The inflatable balloon 220 has a proximal end 222, a distal end 224 and a single lumen inflation chamber 226 made up of a plurality of longitudionally extending interconnected inflation cells 227.

Each inflation cell 227 of inflation chamber 226 is defined by a medial exterior wall 228 and an opposite lateral exterior wall 230 which are sealingly connected along their respective opposed lateral margins 223, 225 to form an inflation cell 227 of inflation chamber 226. Longitudionally extending support members 242 are defined by medial and lateral surfaces 243, 245 and edges 247. Support members 242 are interspersed between inflation cells 227 and are connected to the inflation cells 227 along edges 247 of support members 242 at the lateral margins 223, 225 of inflation cells 227.

The medial exterior wall 228 and medial surface 243 of the inflation cells 227 and support members 242 respectively defines a hollow central lumen 232 of elongated balloon portion 220 shown in FIG. 16. In the expanded configuration, as shown in FIGS. 16–17 central lumen 232 allows for the blood to flow a through blood vessel (not shown) substantially uncompromised and/or unobstructed.

Chamber inflation means is provided and is in continuous fluid connection with inflation cells 227 of inflation chamber 226. In the embodiment shown in FIGS. 16 chamber inflation means is comprised of a low profile elongated flexible tube 212 of a predetermined length and diameter and having a proximal end (not shown) which opens and communicates with the lumen of tube 212 and a distal end 218 which is in fluid communication with inflation chamber 226. As can be appreciated, the length and the diameter of tube 212 can vary depending upon the size of the blood vessel or other tissue conduit in which the device is to be deployed. Further, the length and the diameter of tube 212 can vary depending upon the distance between the point of entry into the vessel or conduit and the preselected site site where device 210 is to be deployed.

Still referring to FIGS. 16–19 micropores or a selectively means (micropores or a selectively permeable membrane) are provided on a selected one of the medial exterior wall 228 or the lateral exterior wall 230 of inflation cells 227 depending upon the desired location of therapeutic agent delivery and the preselected site for substance delivery. A fluid containing a drug or other therapeutic agent, can be delivered to inflation chamber 226 and to the therapeutic agent delivery means as previously described above.

Means for delivering the device 210 to the preselected site are also provided. In the embodiment shown in FIGS. 16–18, a guidewire or delivery stylet 270 is adapted to be removably disposed through the central lumen 232, and is comprised of a proximal end or tip (not shown), a proximally located neck portion 272 and a distally located head portion 274 which terminates in tip 275. Middle portion 276 interconnects neck portion 272 and head portion 274. Retaining means are located on the middle portion 276 for removably securing device 210 to stylet 270.

Referring to FIG. 16, the retaining means on the middle portion 276 of stylet 210 can comprised of a central body 277 which terminates in retaining shoulders 278, 279 at the respective proximal and distal ends of middle portion 276. Central body 277 of the middle portion 276 has a diameter slightly less than the diameters of retaining shoulders 278, 279 which retain the device 210 on the delivery stylet 270 in the deflated or pre-deployed state as shown in FIG. 18.

It is desired that the guidewire or delivery stylet 270 be of a low profile and constructed from a material of sufficient stiffness to allow the surgeon to advance the stylet 270 and device 210 through the lumen of a blood vessel or other conbduit to the predetermined oe preselected site for delivery and deployment.

It is also contemplated that the the delivery means for the device 210 shown in FIGS. 16–19 can further comprise a hollow delivery sheath described above with respect to the embodiments shown in FIGS. 1–3. Means for controlling the stylet 270 and the optional sheath can be located adjacent the proximal end or tip (not shown) of stylet 270 as set forth above.

Inflation of inflation chamber 226 allows the lateral exterior walls 230 of inflation cells 227 to come into retaining contact with the luminal surface of the vessel into which device 210 has been deployed. Following inflation of the inflation chamber 226 the physician can then remove stylet 270 from the patient's body leaving the device 210 deployed a at the predetermined site.

For treatment of a target treatment area adjacent the delivery site, the physician can utilize fluid containing a desired substance, e.g., a drug or other therapeutic agent in the manner set forth above. Depending upon the size or number of pores, the permeability of the membrane, the delivery rate (pressure) of the fluid and the concentration of the therapeutic agent in the fluid, the amount of therapeutic agent delivered to the preselected site or tartget treatment area can be precisely controlled to achieve a desired effect.

Referring generally now to FIGS. 10–15, the present invention also provides a removable, expandable, non-occlusive, dual chambered endovascular support device 310 adapted for providing prolonged localized delivery of a therapeutic agent to a preselected site within a blood vessel 360. Device 310 is comprised of an inflatable, elongated, tubular-shaped balloon 320 having a proximal end 322, a distal end 324 and a central lumen 332. A first or medial inflation chamber 346 is comprised of the medial exterior wall 328 which further defines the central lumen 332 and an opposite dividing wall 329 interconnected at the proximal and distal ends 322, 324.

A second or lateral inflation chamber 348 is coaxially disposed about the medial chamber 346. Lateral inflation chamber is defined by the dividing wall 329 medially, and an opposite lateral exterior wall 330 interconnected at the proximal and distal ends 322,324. Device 310 further comprises medial chamber inflation means which is in fluid connection with the medial chamber 346 and a lateral chamber inflation means which is in fluid connection with the lateral chamber 348. Therapeutic agent delivery means is located on a selected one of the medial exterior wall 328 or the lateral exterior wall 330.

Figure 10:
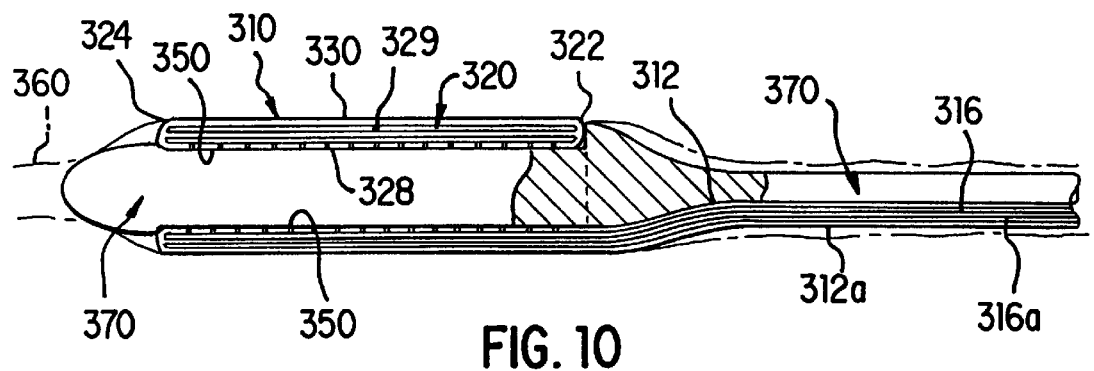
FIG. 10 is a longitudinal cross-sectional view of one embodiment depicting the device having deflated medial and lateral inflation chambers with drug delivery means located on the medial exterior wall mounted on a deployment catheter within an artery prior to deployment.
Figure 11:
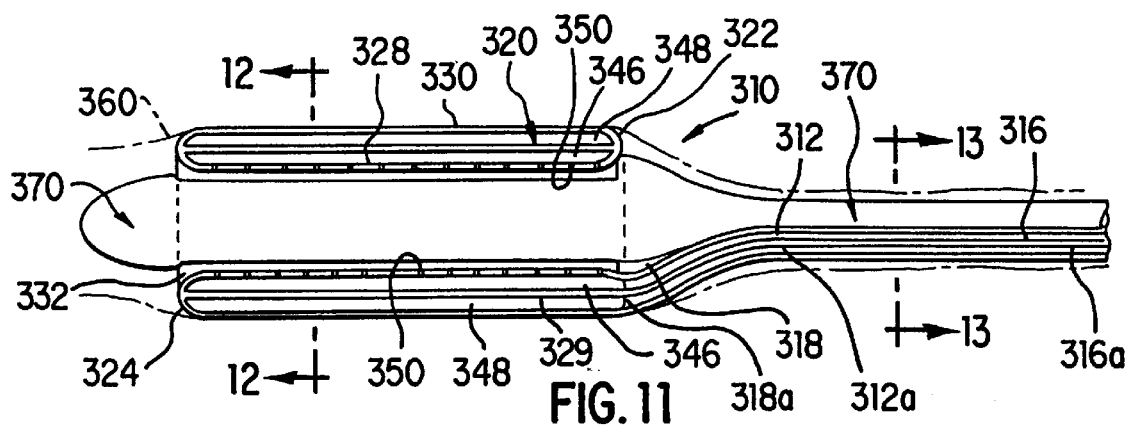
FIG. 11 is a longitudional cross-sectional view of the embodiment shown in FIG. 10 with the medial and lateral inflation chambers inflated.
Figure 14:
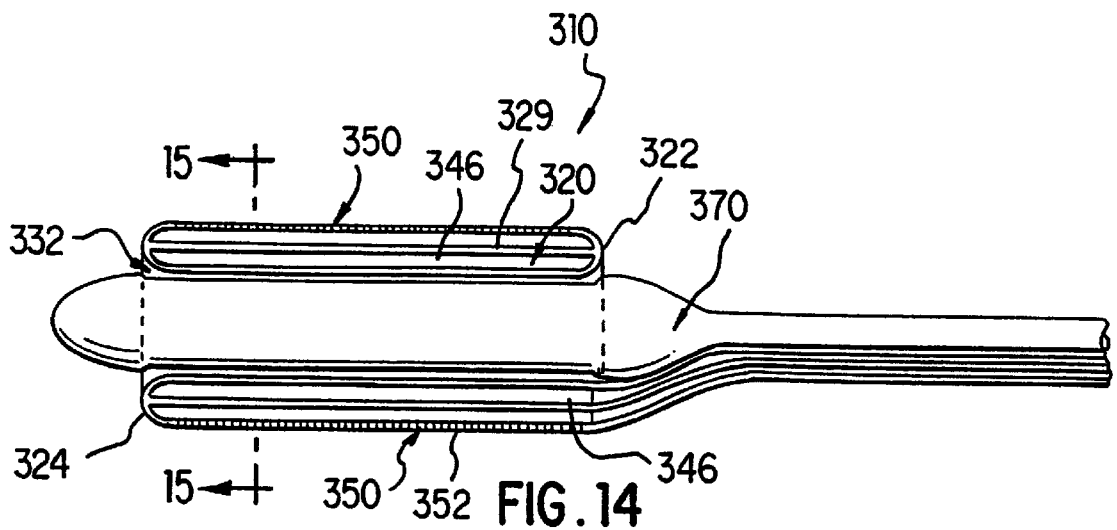
FIG. 14 is a longitudinal cross-sectional view of an alternate embodiment to that shown on FIGS. 10–13 depicting a configuration of the device having inflated medial and lateral inflation chambers with drug delivery means located on the lateral exterior wall mounted on a deployment catheter.
Figure 15:
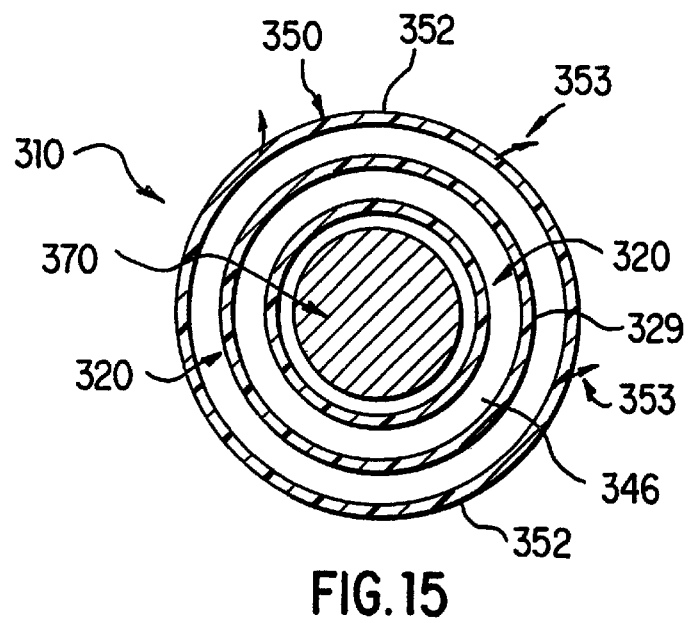
FIG. 15 is a cross-sectional view of the device shown in FIG. 14 taken along lines 15—15 in FIG. 14

In the embodiment shown in FIGS. 10,11 and 14 the medial and lateral chamber inflation means are comprised of low profile elongated flexible tubes 312, 312a each having a predetermined length and diameter and having proximal ends (not shown) which open and communicate with the respective lumens 316, 316a of tubes 312, 312a. The distal ends 318, 318a of flexible tubes 312, 312a are is in fluid communication with the medial and lateral inflation chambers 346, 348 respectively. As with the embodiments set forth above, the length and the diameter of tubes 312, 312a will vary, of course, depending upon the size of the blood vessel and the distance between the point of entry therein and the preselected site site where balloon 320 of device 310 is to be deployed.

A therapeutic agent delivery means 350 is provided on a selected one of the medial exterior wall 328 (see, FIG. 12) or the lateral exterior wall 330 (see, FIG. 14) depending upon the desired location of the preselected site. In the embodiment shown in FIG. 14, for example, the therapeutic agent delivery means is located on the lateral exterior wall 330.

Means for delivering the device 310 to the preselected site are also provided by the invention. In the embodiment shown in FIGS. 10, 11, and 14, a guidewire or delivery stylet 370 similar to the ones previously described is provided.

Figure 12:
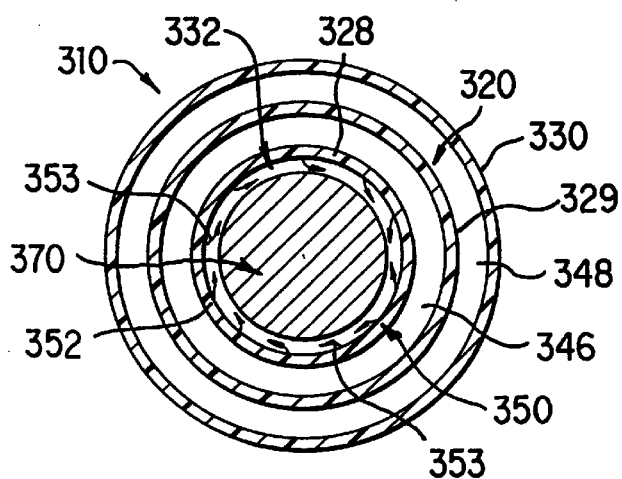
FIG. 12 is a cross-sectional view of the embodiment shown in FIGS. 10–13 taken along lines 12—12 in FIG. 11 with micropores for therapeutic agent delivery located on the medial exterior wall.
Figure 13:
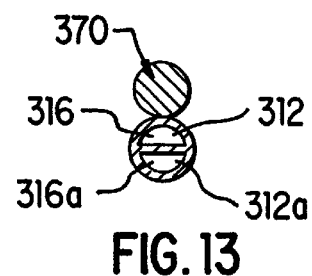
FIG. 13 is a cross-sectional view of the embodiment shown in FIGS. 10–12 taken along lines 13—13 in FIG. 11.

In a preferred embodiment, as depicted in FIG. 14 the therapeutic agent delivery means can comprise a plurality of micropores 52 or a selectively permeable membrane as set forth above located in the lateral exterior wall 330 for therapeutic agent 353 (arrows) delivery directly into the luminal surface of the blood vessel (not shown) at the deployment site. Alternatively, (as shown in FIG. 12) micropores 352 or a selectively permeable membrane can be positioned in the medial exterior wall 328 for delivery of the therapeutic agent directly into the boundary layer of blood flowing through the blood vessel (i.e., the layer of fluid flow adjacent the luminal surface of the blood vessel into which the device 310 is deployed for delivery to a preselected site distal to the deployment site, e.g, when the blood vessel is an artery.

It is specifically contemplated by the invention that the linear and or radial expansion of the device 310 can be controlled by limiting expansion of one or more of the medial, lateral or dividing walls 328, 330, 329. In particular, the invention provides for a selected one of the medial or lateral walls 328, 330 to expand to a predetermined length and diameter in response to a preselected amount of an inflation fluid pressure applied to the lateral chamber 348 by the lateral chamber inflation means. Additionally, the invention provides an embodiment wherein the dividing wall 329 expands to a predetermined length and diameter in response to a preselected amount of an inflation fluid pressure applied to a selected one of the medial or lateral chambers 346, 348 by the corresponding medial or lateral chamber inflation means.

The embodiment depected by FIGS. 10–15 is loaded upon delivery stylet 370 and delivered to the preselected or predetermened endovascular site in the same manner as previously described herein. However, expansion and deployment of device 310 can be accomplished by inflation of either the medial or lateral chambers 346,348 depending upon the desired location of drug delivery and the configuration of device 310.

For example, if boundary layer drug delivery is desired, device 310 is configured such that the therapeutic agent delivery means 350 (micropores 352 or the selectively permeable membrane) is located on the medial exterior wall 328 and deployment is accomplished by inflation of the lateral chamber 348. As the lateral chamber 348 is inflated and expanded the lateral exterior wall 330 comes into retaining contact with the luminal surface of the patient's blood vessel. Alternatively, if drug delivery directly into the luminal surface of the blood vessel at the deployment site is desired, the device is configured such that the therapeutic agent delivery means 350 is located on the lateral exterior wall 330 and the medial chamber 346 is inflated or expanded to bring the lateral exterior wall 330 into retaining contact with the luminal surface of the blood vessel. The therapeutic agent is then infused into the lateral chamber 348. The amount of pressure and flow rate of the fluid infused into the lateral chamber will vary depending upon the size of the pores or the diffusion rate through the membrane and the desired amount of the selected therapeutic agent and the like. The skilled artisan can optimize the dosage or delivery regimen given the teachings provided herein and known in the art.

Referring now to FIGS. 20–21, also provided by the invention is a removable, non-occlusive, endovascular support device 410 that is likewise adapted for prolonged localized delivery of a therapeutic agent at a preselected site within a blood vessel. Device 410 is comprised of a tubular-shaped, dual-chambered, expandable member 420 having a proximal end 422, a distal end 424, an exterior surface 430 and an interior surface 428 which further defines a central lumen 432. Device 410 further comprises a support chamber 426 formed from a plurality of inflatable interconnecting inflation cells 427 and a tubular-shaped therapeutic agent delivery chamber or tube 412 interspersed between the inflation cells 427. Delivery chamber or tube 412 further has an outside surface 436 with a medial face 438 and a lateral face 440 defined by the exterior and interior surfaces 428, 430 respectively of the tubular-shaped member 420.

A means for inflation of the support chamber 426 is provided which is in fluid connection with the support chamber 426. As shown in FIG. 20, the support chamber inflation means is a low profile elongated inflation fluid supply tube 413 having a proximal end (not shown) and a distal end 415 in fluid communication with the proximal end of the support chamber 426.

The therapeutic agent delivery tube 412 is a continuous tube which is interspersed between the various inflation cells 427 and having a closed distal end (not shown) and an opposite open proximal end (not shown) which is in fluid communication with the lumen of the tube 412.

As shown in FIG. 21, also provided is a delivery sheath 464 having a distal end 465. In the pre-deployment or compressed (delivery) configuration shown in FIG. 21, sheath 464 completely encompases device 410 except for the proximal ends of therapeutic agent delivery tube 412 and inflation supply tube 413 (not shown). Fracture lines 466 are provided adjacent the distal end 465 of sheath 464.

In use, the device 410 contained within sheath 464 is advanced to the predetermined or preselected site within the patient's blood vessel. To deploy the device 410, the surgeon grasps the proximal ends of the therapeutic agent delivery tube 412 and the inflation supply tube 413 in one hand and the proximal end of sheath 464 in the other hand. Slight proximally directed pressure is applied to sheath 464 while maintaining a steady state or applying a slightly distally directed pressure to the proximal end of device 410. The opposing directions of force cause the fracture lines 466 in the distal end 465 of sheath 464 to rupture thereby releasing the device 410 from the distal end 465 of sheath 464. Sheath 464 is then withdrawn proximally over the supply tubes and removed from the patient's body. Inflation (deployment) and therapeutic agent delivery can then proceed as previously described and set forth herein.

It can be appreciated by the skilled artisan that the devices described herein can also be utilized in a dual functioning capacity to provide endovascular support to maintain vessel patency as well as to deliver a therapeutic agent. It is contemplated that the devices of the invention will be particularly useful in preventing restenosis in PTCA surgical sites and in other areas where temporary stenting is desired, particularity in combination with local, specific drug therapy.

The devices described herein can be fabricated from any resilient biocompatible material including, but not limited to, materials selected from the group consisting of polymer, synthetic rubber, natural rubber, metal and plastic or combinations thereof by methods known in the art. In general, the devices constructed from polymers or rubber can be molded or cast as a single element and can be cast such that a selected portion of the tubular shaped member (e.g, a portion of the tubular shaped balloon 20 or the flexible support members 42, see, FIG. 1) are pre-formed or moulded into the first shape such that the tubular shaped member rests in the first (or memory) pre-deployment position which fits snugly about the central body 77 of delivery stylet 70. Thus, whenever inflation pressure is no longer applied to the inflation chamber 26, the moulded flexible support members 42 tend to return to the pre-deployment configuration to allow for easy withdrawal of the device 10 after use.

The polymers contemplated for use in fabrication of the devices of the invention can be either biodegradable or non-biodegradable polymers or combinations thereof Examples of suitable non-biodegradable polymers include, e.g., polyurethane, polyethylene, polyethylene terephthalate, polytetrafluoroethylene, ethylene vinyl acetate, polyimid, and nylon. Examples of suitable biodegradable polymers include, polylactic acid and polyglycolic acid. Suitable metals for construction of the devices described herein include, but are not limited to, metals selected from the group consisting of stainless steel, and tantalum, platinum and nitinol.

In one embodiment of the invention described above, (FIGS. 1–3) the flexible support members 42 are located within the lumen of inflation chamber 26 and constructed from nitinol (nickel/titanium alloy). Flexible support members can be constructed such that the nitinol in the support members is normally in a first (pre-deployed) position (i.e., the rest or memory position) when the device is at room temperature, e.g., about 23–25° C. In the first position, the support members cause the device to grippingly engage the middle portion 76 of stylet 70 for delivery to the predetermined site as shown in FIG. 1. Flexible support members 42 can be made to assume a second or working (deployed) position (shown in FIG. 3) by exposing the nitinol support members 42 to a fluid having a temperature of between about 40–65° C. but preferably about 55° C.

Exposing the nitinol to a fluid heated to such temperatures causes the metal to expand and straighten so that the flexible support members 42 move from the first position to the second (deployed) position. Typically, the flexible support members 42 are exposed to the heated fluid by infusing the heated fluid through the lumen 16 of the tube 12. Suitable fluids which can be utilized to irrigate the nitinol substance delivery segment include, but are not limited to, fluids selected from the group consisting of ringer's solution, lactated ringer's solution, 5% dextrose solution, 10% dextrose solution, normal saline solution, ½ normal saline solution, 5% dextrose and ½ normal saline solution, and sterile water. These fluids also serve as examples of the fluids which can be utilized to carry a substance to the predetermined site by infusion through the devices as described herein.

The devices described herein specifically provide a means for locally delivering a therapeutic agent to the boundary layer of fluid flowing through any bodily conduit into which they are deployed. For example, the devices described herein can be utilized to provide local drug delivery by utilizing arterial blood flow for prevention or treatment of any disease or condition distal to the site of arterial implantation of the device. Particular examples where the devices of the present invention can be utilized include, but are not limited to, local drug delivery to treat cancer or to maintain perfusion of tissue or organ transplants while the body establishes revascularization of the subject tissue, to prevent restenosis of a PTCA repair or to prevent platelet deposition, coagulation or thrombus formation on a prosthetic device implanted into the cardiovascular system. When the devices described herein are utilized in the cardiovascular system, local delivery of substances is achieved at the predetermined or preselected site without disrupting perfusion of tissues distal to the infusion site.

In particular, the present invention provides a method for providing prolonged localized delivery of a therapeutic agent directly into the boundary layer of blood flowing through a predetermined site in a blood vessel without substantially compromising central blood flow through the vessel (e.g., an artery) comprises the steps of:

a) placing a therapeutic agent delivery device that is adapted to provide prolonged localized delivery of a therapeutic agent directly into the boundary layer of blood flowing through a predetermined site without substantially compromising central blood flow through the vessel adjacent the predetermined site; and b) delivering the therapeutic agent to the predetermined site via the therapeutic agent delivery device.

As contemplated by the present invention, the substance delivered by the devices described herein can be any substance, including any drug, and the device can be used for local delivery of such substances to prevent or treat a variety of disease syndromes or to promote or enhance desired activity within the body. For example, the substance can be an anticoagulant, including but not limited to, heparin, hirudin, hirulog, hirugen, activated and non-activated protein C, synthetic or naturally occurring antagonists of thrombin, and Factor Xa, or other activated or non-activated coagulation protease inhibitors and coagulation factors, e.g., FIX, FVIII, FV, FVIIa and tissue factor.

The devices described herein can also be utilized to deliver a substance which inhibits platelet deposition and thrombus formation or promotes thrombolysis and thrombus dissolution. Examples of such substances include, but are not limited to, plasmin, tissue plasminogen activator (tPA), urokinase (UK), single chain prourokinase (scuPA), streptokinase, prostaglandins, cyclooxygenase inhibitors, phosphodiesterase inhibitors, thromboxane synthetase inhibitors; antagonists of glycoprotein receptors including (GP) Ib,GP IIb/IIIa, antagonists of collagen receptors, and antagonists of platelet thrombin receptors.

Alternatively, the substances delivered by the devices of the present invention can directly affect platelet metabolic function. Examples of such substances include, but are not limited to, prostaglandins, cyclooxygenase inhibitors, phosphodiesterase or thromboxane synthetase inhibitors, inhibitors of calcium transport, or elevators of cyclic adenosine monophosphate (cyclic AMP).

It is also contemplated that the devices of the invention can deliver a substance which prevents restenosis of a blood vessel. Examples of such substances include, but are not limited to, a growth factor, a growth factor inhibitor, growth factor receptor antagonist, transcriptional repressor, translational repressor, antisense DNA, antisense RNA, replication inhibitor, inhibitory antibodies, antibodies directed against growth factors or their receptors, bifunctional molecules comprising a growth factor and a cytotoxin, and bifunctional molecules comprising an antibody and a cytotoxin.

The substance or therapeutic agent delivered by the devices of the present invention can also be a vasodilator, such as nitroglycerin, nitroprusside or other nitric oxide liberators. The vasodilator can also include other suitable vasoactive agents such as beta receptor blocking drugs, inhibitors of intra-cellular calcium transport, prostaglandins, thromboxane antagonists, and the like.

Alternatively, the therapeutic agent can be a radioactive isotope, e.g., selected from the group consisting of a beta particle emitting isotope and a gamma ray or X-ray emitting isotope.

The local drug delivery devices of the present invention can be utilized as the device which is placed into the natural tissue conduit in the methods of local drug delivery described above. The methods of local drug delivery of the present invention can be utilized to deliver any substance into any natural tissue conduit in the mammalian body. The methods described herein are meant to include any substance or drug which can be placed in the lumen of the devices described herein. Certain other embodiments of the invention include methods for locally delivering a substance into a natural tissue conduit in the mammalian body wherein the substances are those substances and drugs previously described herein for preventing or treating restenosis, inhibiting platelet deposition and thrombus formation, promoting thrombolysis, or affecting vascular tone. It is also contemplated that the vasodilators and anticoagulants described herein can be utilized in the methods described above.

Utilizing the methods for predicting downstream concentration of substances (administered by the methods and devices of the present invention) that are taught in the examples, one skilled in the art can determine suitable dosage requirements and treatment regimens for any substance to be delivered to the predetermined site. Dosages and regimens will vary, of course, depending upon the tissue targeted for therapy and upon the particular drug utilized. In particular, the substances for preventing or treating restenosis, inhibiting platelet deposition, and thrombus formation and the vasodilators and anticoagulants described herein can be utilized in the methods for local drug delivery taught herein in amounts determined by the methods taught in the examples and by other optimization procedures known in the art.

One embodiment of the present invention provides a method for locally delivering a substance into a natural tissue conduit wherein the substance inhibits platelet deposition and thrombus formation on a prosthetic cardiovascular device which has been implanted in the cardiovascular system of a subject. The phrase "prosthetic cardiovascular device" includes, but is not limited to, devices such as tubular synthetic grafts, stents, extracorporeal circuits, artificial kidneys, ventricular assist devices, total heart prostheses or oxygenators. As one skilled in the art can appreciate, the method can include, but is not limited to, any of the substances which inhibit platelet deposition and thrombus formation described herein.

The devices and methods of therapy described herein achieve very high drug concentrations locally while minimizing total drug requirements and circulating drug levels, therefore allowing for the efficient use of agents which are available in limited amounts or which could produce side effects. The examples contained herein provide:

1) a theoretical analysis of the convective diffusion problem for the local infusion flow geometry; 2) in vitro studies with measurements of boundary layer drug concentrations distal to infusion sites; and 3) results of studies conducted utilizing a baboon ex vivo shunt system and the local delivery devices of the present invention to block distal thrombus formation.

The examples specifically show that:

1. In typical usage situations drug concentration at the boundary layer of blood near the vessel wall are about 100–1000 times greater than the average drug concentration (averaged over the entire vessel cross section), depending upon the size of the vessel, blood flow conditions and drug diffusivity 2. Local administration of antithrombotic agents reduces total dose requirements (vs. intravenous therapy) by several orders of magnitude for agents having short in vivo half lives, e.g., PPACK antithrombin(D-Phe-Pro-Arg chloromethyl ketone) and nitric oxide.

The following examples document the reproducibility and efficiency of the methods of therapy and the devices described herein.

EXAMPLES

I. Theoretical Analysis

The theoretical problem of predicting downstream wall or boundary layer concentrations of material infused through the luminal wall of a 4 mm i.d. tube having 100 ml/min luminal blood flow, typical of medium-sized and coronary arteries has been solved by the present invention (see also parent application U.S. Pat. No. 5,399,352). In brief, a supercomputer was used to numerically solve the 2-dimensional Navier-Stokes and species conservation equations using a finite volume element program (Fluent, Inc., Lebanon, N.H.). The analysis predicts that when the drug-containing buffer is infused through the wall of the device described herein at a low rate (0.05–0.1 mml/min), then the wall concentration of drug at 1–5 cm downstream will be 10–20% of the drug concentration in the infusate, i.e., infused materials are diluted 80–90%, but achieve wall concentrations 200 times greater than would be obtained by infusing drug uniformly over the entire tube cross section. Infused material is confined to a very thin boundary layer (approximately 250 microns thick) along the tube wall. Wall drug concentration is therefore determined by the volume and concentration of drug infused. Since at higher infusion rates (>1 ml/min) it is possible to nearly saturate the distal vessel wall with infusate, we chose in subsequent experimental studies to infuse highly concentrated reagents at a low rate (0.05–0.1 ml/min) to avoid significant buffer dilution of blood at the vessel wall.

II. In Vitro Studies Demonstrating Boundary Layer Flow Characteristics

In brief, the device utilized in the in vitro studies consisted of a short length (approximately 2 cm) of a standard expanded TEFLON® vascular graft (GORE-TEX®, 30μ internodal distance) having an inner diameter of 4.0 mm. Likewise, for grafts of this type, the preferred range of internodal distance, a measure of porosity, can range from about 10μ to 90μ.

A silicone rubber cuff-reservoir was placed around the graft for infusion of agents through the graft wall, which, therefor, can enter the flow stream only at the portion of the reservoir overlying the graft interface. To study this system in vitro, Evan's blue dye was infused (0.05–0.1 ml/min) with water flow through the device (30 ml/min) scaled for the viscosity difference between water and blood to simulate 100 ml/min blood flow. Dye entered the lumenal space uniformly, around the entire graft circumference. Dye sampling was performed using collection cuffs placed 1–3 cm downstream. Concentration values, obtained by colorimetric analysis, were within 10% of those predicted theoretically (presumably since the experimental flow conditions were not theoretically perfect). Nonetheless, the excellent agreement between theory and experiment confirmed that the theoretical analysis of boundary flow characteristics was accurate.

III. Ex Vivo Studies With Arteriovenous Shunts

To document the efficiency of this boundary layer method of local drug delivery, a local drug delivery device as described herein and provided by the present invention was inserted into the lumen of an extension segment of a baboon femoral arteriovenous shunt and the substance delivery segment was placed 2–3 cm proximal to a segment of highly thrombogenic DACRON® vascular graft material. Blood flow through the extension segment was regulated at 100 ml/min, a value typical of those found in the carotid and iliac arteries of approximately 10 kg baboons. The baboon ev vivo shunt model of DACRON® graft thrombosis, and its usefulness for assessing the effects of antithrombotic therapy, has been described previously (See, e.g., S. R. Hanson, et al., *Arteriosclerosis,* 5: 595–603, (1985); S. R. Hanson, et al, *J Clin Invest,* 81: 149–158, (1988); A. Gruber, et al., Blood, 73: 639–642, (1989); A. Gruber, et al., *Circulation,* 84: 2454–2462, (1991); and W. C. Krupski, et al, *Surgery* 112: 433–440, (1992)).

The agent infused was the antithrombin D-Phe-Pro-Arg chloromethyl ketone (PPACK). This agent was chosen since we have previously studied its effects following intravenous infusion in the same thrombosis model, thereby allowing comparison with the local drug delivery approach. (See, e.g., S. R. Hanson, et al., *Proc Natl Acad Sci USA,* 85: 3184–3188, (1988); A. B. Kelly, et al., *Blood,* 77: 1006–1012, (1991); and S. R. Hanson, et al., *Thrombosis and Hemostasis,* 65(6): 813, (1991)).

Figure 22:
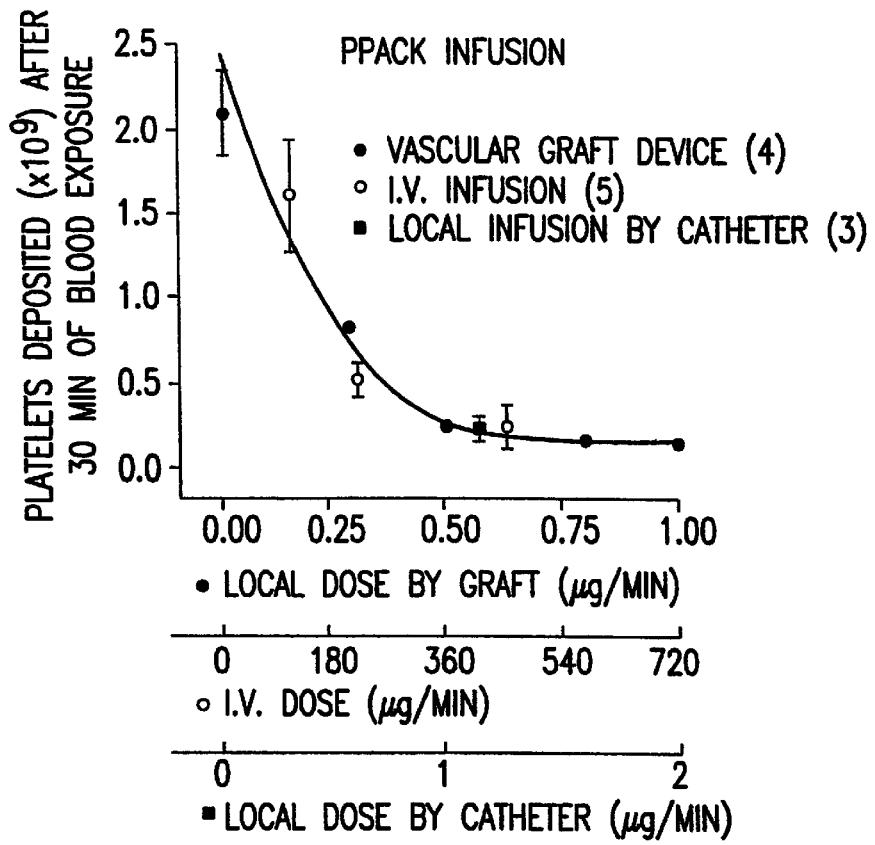
FIG. 22 is a graph showing thrombus inhibition on a DACRON® graft by administration of PPACK in a baboon ex vivo shunt model via conventional systemic intravenous and local infusion routes after 30 minutes of blood exposure.

PPACK was mixed with isotonic saline which was infused at a concentration of 0.1 μg/min. Total platelet deposition was measured over 30 minutes of blood exposure as determined by [111] Indium-platelet imaging. A dose-response curve for local and intravenous (i.v.) administration was virtually coincident for the PPACK infusion. These data imply only that the shape of the i.v. and local infusion dose-response curves for each agent are similar. These data also allow determination of the relative efficiency of i.v. vs. local drug administration. Thus, utilizing the optimization procedures taught herein, the local dose requirement of PPACK for inhibiting platelet thrombus formation was reduced approximately 400-fold (for local infusion vs. systemic i.v. therapy) over 30 minutes of blood exposure (see, FIG. 22). Similarly, laws of first-order clearance kinetics predict that, when agents are infused by the local route, local boundary layer drug concentrations will exceed systemic circulating levels by the same factors (i.e., by 400-fold for PPACK at the 30 minute blood exposure level). This method for predicting dosage requirements can be utilized for other substances to determine an appropriate treatment regimen.

I.V. infusion of PPACK at 45 μg/kg-min into 10 kg baboons having a plasma volume of ~500 ml blocks thrombus formation and produces steady-state plasma levels of>1 μg/ml with an apparent in vivo half life of PPACK of about 2.5 minutes (S. R. Hanson, et al, *Proc Natl Acad Sci USA,* 85: 3184–3188, (1988)). The theoretical and in vitro studies (in the optimization procedures discussed herein) predict that in the shunt study, infusion of PPACK solution (5 μg/ml) at a rate of 0.1 ml/min should achieve a wall concentration of 1–2 μg/ml (i.e., 60–80% dilution of infusate), which is essentially that plasma level previously shown to effectively block thrombus formation in the i.v. infusion studies. These data with PPACK therefore denote that the infused material is effectively concentrated in a boundary layer that occupies only approximately 5% of the cross section of a 4 mm i.d. tube having a total flow of 100 ml/min.

In summary, the boundary layer into which effectively all drug is concentrated 2–3 cm downstream comprises an annular ring at the blood-vessel interface occupying only about 5% of the tube cross-sectional area. Thus, total effective drug requirements at that area will be remarkably small. For example, to maintain local PDGF-BB (platelet derived growth factor) levels at 10 ng/ml, we would infuse PDGF solution (100 ng/ml at 0.05 ml/min (i.e., 90% dilution of infusate) or approximately 7 μg per day, a remarkably small requirement.

Therefore, where standard therapeutic levels are known for a substance administered by conventional i.v. (systemic) therapy, the dosage and treatment regimen for local delivery of the substance utilizing the devices of the present invention can be predicted. Further, while the pharmacokinetics of many agents may be complex, these issuethan serrelevant for agents having half lives less than several hours, since drug recirculation will contribute very little to the boundary layer drug levels. These data indicate that the methods of the present invention have the advantage of providing local drug levels in known quantities to good approximation to target tissues.

IV. Comparison of Substance Delivery Routes

Three approaches for delivery of PPACK to the surface of a thrombogenic DACRON® graft implanted in an ex vivo baboon artero-venous (a-v) shunt were evaluated for their effectiveness at reducing thrombus formation and platelet deposition after 30 minutes of blood exposure to the graft. Blood flow through the ex vivo a-v shunt was controlled at 100 ml/min for each administration. DACRON® grafts are known to actively thrombose if even a portion of the thrombogenic DACRON® surface is exposed to blood flow (See, A. Gruber, et al., *Blood,* 23: 639–642 (1989)). Intravenous systemic administration of PACK at 400 μg/min was necessary to reduce platelet deposition on the DACRON® graft by 90% at 30 minutes of blood exposure (See, FIG. 22).

Figure 23:
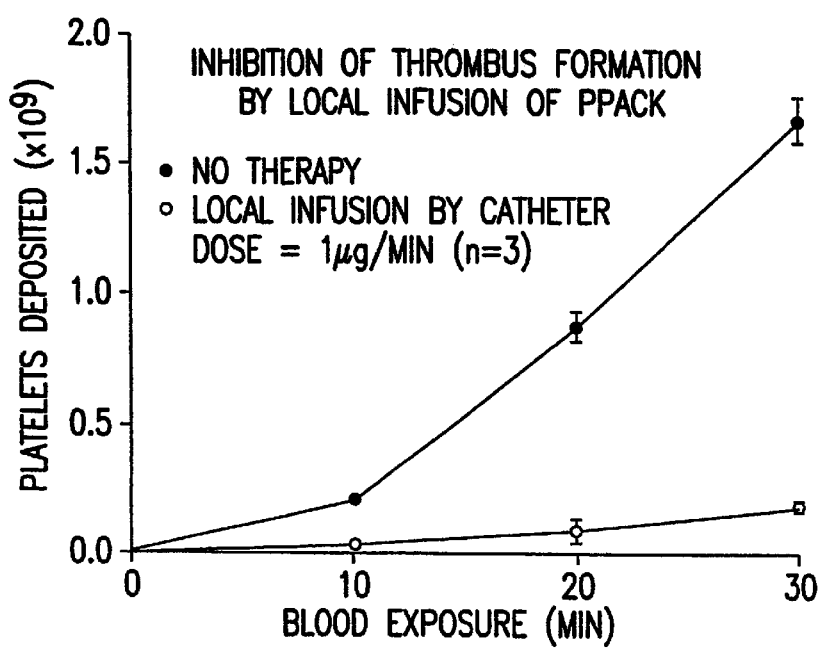
FIG. 23 is a graph showing inhibition of platelet deposition on a DACRON® graft by local infusion of PPACK in a baboon ex vivo shunt model over 30 minutes post blood exposure using the devices described herein.

Local infusion into the boundary layer of blood flow 2–3 cm proximal to the thrombogenic DACRON® graft was accomplished utilizing the model described in Example II above. A local delivery concentration of 0.5 µg/min at 30 minutes of blood exposure was necessary to reduce platelet deposition on the DACRON® graft by 90% (See, FIG. 23).

Local infusion into the boundary layer of blood flow 2–3 cm proximal to the DACRON® graft was also achieved by placement of a local drug delivery device as described herein within the lumen of the ex vivo shunt. Briefly, an indwelling cathater 10 of the type shown in FIG. 1 of parent application, U.S. Pat. No. 5,523,092, having a substance delivery segment was positioned in the lumen of the ex vivo extension segment approximately 2–3 cm proximal to the target delivery site (i.e the DACRON® graft) as is similarly depicted in the instant FIG. 3 which shows the device 10 deployed proximal to an area of arterial stenosis 56. The coiled configuration of the substance delivery segment and position of the substance delivery holes provided for delivery of infused PPACK directly into the boundary layer of blood flowing through the ex vivo shunt proximal to the DACRON® graft. The PPACK was infused through the infusion port through the lumen of the tube through the substance delivery holes and into the lumen of the ex vivo shunt (not shown). Infusion of PPACK at a rate of 1 µg/min effectively reduced thrombus formation on the DACRON® graft by 90% as compared to controls at 30 minutes of blood exposure. (See, FIG. 22)

Platelet deposition on the DACRON® graft surface was measured over 30 minutes in ex vivo shunts in two groups. The graft surface in one group of 3 animals was treated with local delivery of PPACK by infusion utilizing the indwelling catheters described herein at a rate of 1 µg/min. This data was compared to a second group consisting of 21 control animals (see, FIG. 23). Platelet deposition was measured as previously described using[111]Idium-platelet imaging. Platelets accumulated on the surface of the DACRON® graft in an exponential fashion in the control (untreated) animals. Treated animals (PPACK 1 µg/min), however, showed a 90% reduction in (or inhibition of) platelet deposition over 30 minutes.

These data indicate that the indwelling local delivery catheters provided by the present invention show excellent correlation to the boundary flow data as predicted in the theoretical analysis (Example I) and demonstrated in the in vitro local delivery data (Example II). Moreover, the catheter infusion approach reduced the therapeutic drug requirement by a factor of at least 400 times that required by conventional intravenous systemic administration.

Additional references and data co-authored by at least one of the co-inventors of the present invention also demonstrate the efficacy of localized drug delivery utilizing the boundary layer delivery methods provided by the invention.

V. Local Infusion of Nitric Oxide

1. Saavedra J E, Southan G, Davies K, Lundell A, Markou C., Hanson S R, Andrie C, Hurford W E, Zapol W M, Keefer L K: Localizing antithrombotic and vasodilatory activity with a novel, ultrafast nitric oxide donor. J. Med Chem 39: 4361–4365, 1996.
2. Hanson S R, Hutsell T C, Keefer L K, Mooradian D L, Smith D J: Nitric oxide donors: A continuing opportunity in drug design. Adv Pharmacol, 34: 383–398, 1995.
3. Chen C., Hanson S R, Keefer L K, Hutsell T C, Hughes J D, Ku D N, Lumsden A B: Boundary layer infusion of nitric oxide reduces smooth muscle cellproliferation in the endarterectomized canine artery. J. Surg Res 67: 26–32, 1997.

VI. Local Infusion of Heparin

4. Chen C, Hanson S R, Lumsden A B: Boundary layer infusion of heparin prevents thrombosis and reduces neointimal hyperplasia in venous PTFE grafts without systematic anticoagulation. J Vasc Surg 22: 237–247, 1995.
5. Chen C, Hughes J D, Mattar S G, Hanson S R, Lumsden A B: Transgraft infusion of heparin prevents early thrombosis of expanded PTFE grafts in the canine femoral vein. Ann Vasc Surg 10: 147–152, 1996.

VII. Local Infusion of Basic Fibroblast Growth Factor

6. Chen C, Li J, Mattar S G, Pierce G F, Aukerman L, Hanson S R, Lumsden A B: Boundary layer infusion of basic fibroblast growth factor accelerates intimal hyperplasia in endarterectomized canine artery. J Surg Res 69: 300–306, 1997.

VIII. Local Infusion of Fibroblast Growth Factor-Saporin

7. Mattar S G, Hanson S R, Pierce G F, Chen C, Hughes J D, Cook J E, Shen C, Noe B A, Suwyn C R, Scott J R, Lumsden A B: Local infusion of fibroblast growth factor-saporin reduces intimal hyperplasia. J Surg Res 60: 339–344, 1996.
8. Chen C, Mattar S G, Hughes J D, Pierce G F, Cook J E, Ku D N, Hanson S R, Lulmsden A B: Recombinant chimeric toxin, basic fibroblast growth factor-saporin, reduces venous neointinmal hyperplasia in the arteriovenous graft. Circulation, 94: 1989–1955, 1996.

Throughout this application, various publications are referenced. The disclosures of these publications in their entireties are hereby incorporated by reference into this application in order to more fully describe the state of the art to which this invention pertains.

Although the present process has been described with reference to specific details of certain embodiments thereof, it is not intended that such details should be regarded as limitations upon the scope of the invention except as and to the extent that they are included in the accompanying claims.

What is claimed is:

1. A removable, expandable, non-occlusive endovascular support device adapted for providing prolonged localized delivery of a therapeutic agent to a preselected site within a blood vessel, comprising:
   a. an inflatable, elongated, tubular-shaped balloon having a proximal end, a distal end and a central lumen therethrough, the tubular-shaped balloon having an inflation chamber defined by:
      i. a medial exterior wall defining the central lumen;
      ii. an opposite lateral exterior wall; and
      iii. the opposed proximal and distal ends;
   b. chamber inflation means in fluid connection with the inflation chamber; and
   c. therapeutic agent delivery means located on a selected one of the medial exterior wall or the lateral exterior wall.

2. The device of claim 1, wherein the therapeutic agent delivery means comprises a selected one of the medial exterior wall or the lateral exterior wall defining a plurality of micro pores disposed therethrough.

3. The device of claim 2, wherein the micro pores are located in the lateral exterior wall and are juxtaposed to a luminal surface of the blood vessel such that a substance delivered therethrough directly contacts the luminal surface of the blood vessel.

4. The device of claim 2, wherein the micro pores are located in the medial exterior wall such that a substance delivered therethrough is delivered into the boundary layer of blood flowing through the blood vessel.

5. The device of claim 1, wherein the therapeutic agent delivery means comprises a selectively permeable membrane comprising at least a portion of a selected one of the medial or lateral exterior walls.

6. The device of claim 5, wherein the selectively permeable membrane is located in the lateral exterior wall and is juxtaposed to a luminal surface of the blood vessel such that a substance delivered therethrough directly contacts the luminal surface of the blood vessel.

7. The device of claim 5, wherein the selectively permeable membrane is located in the medial exterior wall such that a substance delivered therethrough is delivered into the boundary layer of blood flowing through the blood vessel.

8. The device of claim 5, wherein the selectively permeable membrane is comprised of a biocompatible material selected from the group consisting of a biodegradable polymer, a non-biodegradable polymer, a nylon and a porous metal alloy.

9. The device of claim 8, wherein the selectively permeable membrane is a non-biodegradable polymer selected from the group consisting of polytetrafluoroethylene, ethylene vinyl acetate, polyethylene, and polyethylene terephthalate.

10. The device of claim 1, wherein the predetermined site is the boundary layer of blood flowing through the blood vessel upstream of a target treatment area.

11. The device of claim 1, wherein the chamber inflation means comprises a low profile elongated inflation fluid supply tube in fluid communication with the proximal end of the inflation chamber.

12. The device of claim 1, further comprising support means for maintaining a predetermined shape of the balloon located within a selected one of the medial exterior wall, the lateral exterior wall or the inflation chamber.

13. The device of claim 12, wherein the support means further comprises a flexible support member of suitable stiffness so as to maintain the device in a predetermined shape upon deployment of the device at the preselected site.

14. The device of claim 13, wherein the flexible support member is comprised of a material selected from the group consisting of a metal, a plastic, a polymer, and a ceramic.

15. The device of claim 13, wherein the flexible support member extends radially within a selected one of medial exterior wall, the lateral exterior wall or the inflation chamber.

16. The device of claim 13, wherein the flexible support member extends longitudinally within a selected one of medial exterior wall, the lateral exterior wall or the inflation chamber.

17. The device of claim 1, wherein the medial exterior wall expands to a predetermined length and diameter in response to a preselected amount of an inflation fluid pressure applied to the inflation chamber by the chamber inflation means.

18. The device of claim 1, wherein the lateral exterior wall expands to a predetermined length and diameter in response to a preselected amount of inflation fluid pressure applied to the inflation chamber by the chamber inflation means.

19. The device of claim 1, wherein the inflation chamber inflates to a predetermined length along a longitudinal axis defined by the central lumen in response to a preselected amount of inflation fluid pressure applied to the inflation chamber by the chamber inflation means.

20. The device of claim 1, wherein the inflation chamber inflates to a predetermined diameter along a longitudinal axis defined by the central lumen in response to a preselected amount of inflation fluid pressure applied to the inflation chamber by the chamber inflation means.

21. The device of claim 20, wherein expansion of the inflation chamber to the predetermined length is controlled by a selected one of the medial exterior wall, the lateral exterior wall or a support means for maintaining a predetermined shape of the balloon located within a selected one of the material exterior wall, the lateral exterior wall or the inflation chamber.

22. The device of claim 1, wherein the medial exterior wall is of a predetermined length and a preselected elasticity.

23. The device of claim 1, wherein the lateral exterior wall is of a predetermined length and a preselected elasticity.

24. The device of claim 1, wherein the inflation chamber further comprises a plurality of longitudinally extending interconnected inflation cells disposed among a plurality of substantially non-expandable support members having a predetermined length and stiffness.

25. The device of claim 1, wherein the inflation chamber further comprises a plurality of radially extending interconnected inflation cells disposed among a plurality of substantially non-expandable support members having a predetermined length and stiffness.

26. The device of claim 1, wherein the therapeutic agent is disposed within a fluid supplied to the inflation chamber via the chamber inflation means.

27. The device of claim 1, wherein the therapeutic agent is a drug.

28. The device of claim 1, wherein the therapeutic agent is an anticoagulant selected from the group consisting of D-Phe-Pro-Arg chloromethyl ketone, an RGD peptide-containing compound, heparin, an antithrombin compound, a platelet receptor antagonist, an anti-thrombin antibody, an anti-platelet receptor antibody, aspirin, a prostaglandin inhibitor, a platelet inhibitor and a tick anti-coagulant peptide, and combinations thereof.

29. The device of claim 1, wherein the therapeutic agent is a promoter of vascular cell growth selected from the group consisting of a growth factor stimulator, a growth factor receptor agonist, a transcriptional activator, and a translational promoter, and combinations thereof.

30. The device of claim 1, wherein the therapeutic agent is an inhibitor of vascular cell growth selected from the group consisting of a growth factor inhibitor, a growth factor receptor antagonist, a transcriptional repressor, a translational repressor, an antisense DNA, an antisense RNA, a replication inhibitor, an inhibitory antibody, an antibody directed against growth factors, a bifunctional molecule consisting of a growth factor and a cytotoxin, and a bifunctional molecule consisting of an antibody and a cytotoxin, and combinations thereof.

31. The device of claim 1, wherein the therapeutic agent is selected from the group consisting of a cholesterol-lowering agent, a vasodilating agent, and agents which interfere with endogenous vasoactive mechanisms, and combinations thereof.

32. The device of claim 1, wherein the therapeutic agent is a smooth muscle inhibitor selected from the group consisting of an agent that modulates intracellular calcium binding proteins, a receptor blocker for contractile agonists, an inhibitor of the sodium/hydrogen antitransporter, a protease inhibitor, a nitrovasodilator, a phosphodiesterase inhibitor, a phenothiazine, a growth factor receptor agonist, an anti-mitotic agent, an immunosuppressive agent, and a protein kinase inhibitor, and combinations thereof.

33. The device of claim 1, wherein the therapeutic agent is a radioactive isotope.

34. The device of claim 1, wherein the radioactive isotope is selected from the group consisting of a beta particle emitting isotope and a gamma particle emitting isotope.

35. The device of claim 1, further comprising means for delivering the device to the preselected site comprised of:
   a. a delivery stylet adapted to be removably disposed through the central lumen, comprised of a neck portion having a proximal tip, a distal tip and a middle portion interconnecting the neck portion and distal tip;
   b. retaining means located on the middle portion for removably securing the device to the stylet; and
   c. means adjacent the proximal tip for controlling the delivery of the device within the vessel at the predetermined site.

36. A removable, expandable, adapted for providiascular support device adapted for providing prolonged localized delivery of a therapeutic agent to a preselected site within a blood vessel, comprising:
   a. an inflatable, elongated, tubular-shaped balloon having a proximal end, a distal end and a central lumen therethrough, comprising:
      i. a medial chamber comprised of a medial exterior wall defining the central lumen and an opposite dividing wall interconnected at the proximal and distal ends, and
      ii. a lateral chamber coaxially disposed about the medial chamber comprised of the dividing wall, and an opposite lateral exterior wall interconnected at the proximal and distal ends;
   b. medial chamber inflation means in fluid connection with the medial chamber;
   c. lateral chamber inflation means in fluid connection with the lateral chamber; and
   d. therapeutic agent delivery means located on a selected one of the medial exterior wall or the lateral exterior wall.

37. The device of claim 36, wherein the therapeutic agent delivery means comprises a selected one of the medial exterior wall or the lateral exterior wall defining a plurality of micro pores disposed therethrough.

38. The device of claim 36, wherein the micro pores are located in the lateral exterior wall and are juxtaposed to a luminal surface of the blood vessel such that a substance delivered therethrough directly contacts the luminal surface of the blood vessel.

39. The device of claim 38, wherein the micro pores are located in the medial exterior wall such that a substance delivered therethrough is delivered into the boundary layer of blood flowing through the blood vessel.

40. The device of claim 36, wherein the therapeutic agent delivery means comprises a selectively permeable membrane comprising at least a portion of a selected one of the medial or lateral exterior walls.

41. The device of claim 40, wherein the selectively permeable membrane is located in the lateral exterior wall and are juxtaposed to a luminal surface of the blood vessel such that a substance delivered therethrough directly contacts the luminal surface of the blood vessel.

42. The device of claim 40, wherein the selectively permeable membrane is located in the medial exterior wall such that a substance delivered therethrough is delivered into the boundary layer of blood flowing through the blood vessel.

43. The device of claim 40, wherein the selectively permeable membrane is comprised of a biocompatible material selected from the group consisting of a biodegradable polymer, a non-biodegradable polymer, a nylon and a porous metal alloy.

44. The device of claim 43, wherein the selectively permeable membrane is a non-biodegradable polymer selected from the group consisting of polytetrafluoroethylene, ethylene vinyl acetate, polyethylene, polyethylene terephthalate, and polyurethane.

45. The device of claim 36, wherein the predetermined site is the boundary layer of blood flowing through the blood vessel upstream of a target treatment area.

46. The device of claim 36, wherein the medial chamber inflation means comprises a low profile elongated inflation fluid supply tube in fluid communication with the proximal end of the medial chamber.

47. The device of claim 36, wherein the lateral chamber inflation means comprises a low profile elongated inflation fluid supply tube in fluid communication with the proximal end of the lateral chamber.

48. The device of claim 36, further comprising means for delivering the device to the preselected site comprised of:
   a. a delivery stylet adapted to be removably disposed through the central lumen, comprised of a proximal tip, a distal tip and a middle portion interconnecting the proximal and distal tips;
   b. retaining means located on the middle portion for removably securing the device to the stylet; and
   c. means for controlling the delivery of the device within the vessel at the predetermined site.

49. The device of claim 36, wherein the medial wall expands to a predetermined diameter in response to a preselected amount of an inflation fluid pressure applied to the medial chamber by the medial chamber inflation means.

50. The device of claim 36, wherein the dividing wall expands to a predetermined length and diameter in response to a preselected amount of an inflation fluid pressure applied to a selected one of the medial or lateral chambers by the corresponding medial or lateral chamber inflation means.

51. The device of claim 36, wherein the lateral wall expands to a predetermined length and diameter in response to a preselected amount of an inflation fluid pressure applied to the lateral chamber by the lateral chamber inflation means.

52. The device of claim 36, wherein the therapeutic agent is disposed within a fluid supplied to a selected one of said medial or lateral chambers via the medial or lateral chamber inflation means.

53. The device of claim 36, wherein the therapeutic agent is a drug.

54. The device of claim 36, wherein the therapeutic agent is an anticoagulant selected from the group consisting of D-Phe-Pro-Arg chloromethyl ketone, an RGD peptide-containing compound, heparin, an antithrombin compound, a platelet receptor antagonist, an anti-thrombin antibody, an anti-platelet receptor antibody, aspirin, a prostaglandin inhibitor, a platelet inhibitor and a tick anti-platelet peptide, and combinations thereof.

55. The device of claim 36, wherein the therapeutic agent is a promoter of vascular cell growth selected from the group consisting of a growth factor stimulator, a growth factor receptor agonist, a transcriptional activator, and a translational promoter, and combinations thereof.

56. The device of claim 36, wherein the therapeutic agent is an inhibitor of vascular cell growth selected from the group consisting of a growth factor inhibitor, a growth factor receptor antagonist, a transcriptional repressor, a translational repressor, an antisense DNA, an antisense RNA, a replication inhibitor, an inhibitory antibody, an antibody directed against growth factors, a bifunctional molecule consisting of a growth factor and a cytotoxin, and a bifunctional molecule consisting of an antibody and a cytotoxin, and combinations thereof.

57. The device of claim 36, wherein the therapeutic agent is selected from the group consisting of a cholesterol-lowering agent, a vasodilating agent, and agents which interfere with endogenous vasoactive mechanisms, and combinations thereof.

58. The device of claim 36, wherein the therapeutic agent is a smooth muscle inhibitor selected from the group consisting of an agent that modulates intracellular calcium binding proteins, a receptor blocker for contractile agonists, an inhibitor of the sodium/hydrogen antitransporter, a protease inhibitor, a nitrovasodilator, a phosphodiesterase inhibitor, a phenothiazine, a growth factor receptor agonist, an anti-mitotic agent, an immunosuppressive agent, and a protein kinase inhibitor, and combinations thereof.

59. The device of claim 36, wherein the therapeutic agent is a radioactive isotope.

60. The device of claim 36, wherein the radioactive isotope is selected from the group consisting of a beta particle emitting isotope and a gamma particle emitting isotope.

61. A removable, non-occlusive, endovascular support device adapted for prolonged localized delivery of a therapeutic agent at a preselected site within a blood vessel, comprising:

a. a tubular-shaped, dual-chambered, expandable member having a proximal end, a distal end, an exterior surface and an interior surface defining a central lumen therethrough, comprising:

i. a support chamber formed from a plurality of inflatable interconnecting inflation cells; and ii. a tubular-shaped therapeutic agent delivery chamber interspersed between the inflation cells and having an outside surface with a medial face and a lateral face defined by the exterior and interior surfaces respectively of the tubular-shaped member;

b. support chamber inflation means in fluid connection with the support chamber;

c. a therapeutic agent delivery tube in fluid connection with the therapeutic agent delivery chamber; and d. therapeutic agent delivery means located on a selected one of the medial or lateral surfaces of the therapeutic agent delivery chamber.

62. The device of claim 61, wherein the therapeutic agent delivery means comprises a selected one of the medial exterior wall or the lateral exterior wall defining a plurality of micro pores disposed therethrough.

63. The device of claim 61, wherein the support chamber inflation means comprises a low profile elongated inflation fluid supply tube in fluid communication with the proximal end of the support chamber.

64. The device of claim 61, further comprising means for delivering the device to the preselected site comprised of:

a. a delivery stylet adapted to be removably disposed through the central lumen, comprised of a proximal tip, a distal tip and a middle portion interconnecting the proximal and distal tips;

b. retaining means located on the middle portion for removably securing the device to the stylet; and c. means for controlling the delivery of the device within the vessel at the predetermined site.

65. The device of claim 61, further comprising a removable delivery or deployment sheath coaxially disposed about and covering at least a portion of the device.

* * * * *